US006174867B1

(12) United States Patent
Hindsgaul

(10) Patent No.: US 6,174,867 B1
(45) Date of Patent: *Jan. 16, 2001

(54) 1-GALACTOSE DERIVATIVES HAVING A CARBON- OR NITROGEN-CONTAINING AGLYCON LINKAGE

(75) Inventor: Ole Hindsgaul, Edmonton (CA)

(73) Assignee: Synsorb Biotech, Inc., Calgary (CA)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/075,427

(22) Filed: May 8, 1998

(51) Int. Cl.$^7$ ..................................................... A61K 31/70
(52) U.S. Cl. .............................................................. 514/42
(58) Field of Search ................................. 514/23, 24, 25, 514/42; 536/4.1, 22.1, 29.1, 122, 124, 18.5, 18.6

(56) References Cited

U.S. PATENT DOCUMENTS

| | | | |
|---|---|---|---|
| 4,137,401 | 1/1979 | Lemieux et al. | 536/116 |
| 5,580,858 | 12/1996 | Ippolito et al. | 514/25 |
| 5,932,554 | * 8/1999 | Hindsgaul | 514/24 |

FOREIGN PATENT DOCUMENTS

| | | |
|---|---|---|
| 0 649 021 | 4/1995 | (EP) . |
| 94/19360 | 9/1994 | (WO) . |
| 95/21628 | 8/1995 | (WO) . |
| 9639189 | 12/1996 | (WO) . |
| 9639190 | 12/1996 | (WO) . |
| 9639191 | 12/1996 | (WO) . |
| 9821220 | 5/1998 | (WO) . |
| 9821221 | 5/1998 | (WO) . |
| 9821222 | 5/1998 | (WO) . |

OTHER PUBLICATIONS

Hindsgaul et al., "Immobilization of Reducing Sugars as Toxin Binding Agents", Bioconjugate Chemistry, vol. 8: 466–471, 1997.*
Spangler, B. D., "Structure and Function of Cholera Toxin and Related *Escherichia coli* Heat–Labile Enterotoxin", *Microbiological Reviews*, 56(4):622–647 (1992).
Hol, W. G. J., et al., "Structure and Function of *E. coli* Heat–Labile Enterotoxin and Cholera Toxin B Pentamer", *Bacterial Toxins and Virulence Factors in Disease*, Ed. by J. Moss et al., Marcel Dekker, Inc. (1995).
Evans et al., *J. Amer. Chem. Soc.*, 112:4011–4030 (1990).
Pu et al., *J. Org. Chem.*, 56:1280–1283 (1991).
Williams et al., *J. Amer. Chem. Soc.*, 113:9276–9286 (1991).
Maarten H. D. Postema, "Recent Developments in the Synthesis of C–Glycosides" *Tetrahedron*, vol. 48, No. 40, pp. 8545–8599 (1992).
O. R. Martin et al., *J. Org. Chem.* 1990, 55, 5188–5190.
Chemical Abstract No. 96: 218145e, corresponding to L. Petrus et al., *Chem zvesti* 1982, 36, 103.

A. Förtsch et al., *Carbohydr. Res.* 1987, 164, 391.
Y. Araki et al., *Tetrahedron Lett.* 1987, 28, 5853.
B. Giese et al., *Angew. Chem. Intl. Ed. Engl.* 1986, 25, 450.
Norberg et al., *Carbohydr. Res.* 1988, 183, 71.
R. M. Williams et al., *Tetrahedron Lett.* 1983, 27, 2715.
A. O. Stewart et al., *J. Am. Chem. Soc.* 1985, 107, 4289.
D. S. Brown et al., *Tetrahedron Lett.* 1989, 45, 4293.
K. Narasaka et al., *Chem. Lett.* 1987, 2139.
S. Murata et al., *Tetrahedron Lett.* 1982, 25, 2601.
T. Mukaiyama et al., *Carbohydr. Res.* 1987, 171, 71.
M. Shimizu et al., *Chem. Lett.* 1984, 1531.
M. G. Hoffman et al., *Liebigs Ann. Chem.* 1985, 2403.
P. Allevi et al., *J. Chem. Soc., Chem. Commun.* 1987, 101.
Kagen et al., *Synlett*, 1990, 643–650.
M. Dubois et al., *Anal. Chem.*, 28, (1979) 350–356.
H. H. Westal et al., "Methods of Enzymology," 34(b), 64 (1974).
Svennerholm, A–M. et al., *Current Microbiology*, 1:19–23 (1978).
D.W.K. Acheson et al., *Infect. Immun.*, 61 (3), 1098–1104 (1993); and corresponding Chem. Abstract No. 118: 226797g.
A. Ramesh et al., *J. Biotechol.*, 43(1), 45–51 (1995); and corresponding Chem. Abstract No. 124: 7117f.
P. Fugedi et al., *Glycoconjugate Journal*, 4, 97–100 (1987).
E. Bar–Guilloux et al., *Carbohydrate Research*, 250(1), 1–8 (1993).
M. Cerny et al., *Collection of Czechoslovak Chemical Communications*, 61(10), 1489–1500 (1996).
G. Vic et al., *Tetrahedron: Asymmetry*, 5(12), 2513–1516 (1994).
J. DeFaye et al., *Carbohydrate Research*, 253, 185–194 (1994).
I. Tvaroska et al., *Carbohydrate Research*, 229 (2), 225–231 (1992).
M.–O. Contour–Galcera et al., *Carbohydrate Research*, 281 (1), 99–118 (1996).
M. Petrusova et al., *Carbohydrate Research*, 283, 73–80 (1996).M. Petrusova et al., *Carbohydrate Research*, 283, 73–80 (1996).
Witczak, Z.J. et al., Synthesis of L–Fucopyranosyl, 4–Thiodisacchasrides from Levoglucosenone and Their Inhibitory Activity on α–L–Fucosidase, "Bioorganic & Medicinal Chemistry Letters", vol. 5, No. 18:2169–2174, 1995.
M. Carcano et al., *J. Chem. Soc., Chem. Comm.*, 1989, 297–298.

* cited by examiner

Primary Examiner—Howard C. Lee
(74) Attorney, Agent, or Firm—Burns, Doane, Swecker & Mathis LLP

(57) ABSTRACT

Disclosed are novel 1-galactose derivatives having a carbon- or nitrogen-containing aglycon linkage. The disclosed compounds inhibit binding of toxins, such as heat-labile enterotoxin or cholera toxin, to their receptors either in vitro or in vivo. The disclosed compounds also inhibit binding of enterovirulent organisms (e.g., bacteria, virus, fungi, and the like), such as *Vibrio cholerae* and enterotoxigenic strains of *Escherichia coli*, to their cell surface receptors.

64 Claims, 2 Drawing Sheets

1-GALACTOSE DERIVATIVES HAVING A CARBON- OR NITROGEN-CONTAINING AGLYCON LINKAGE

BACKGROUND OF THE INVENTION

1. Field of the Invention

This invention relates to novel 1-galactose derivatives having a carbon- or nitrogen-containing aglycon linkage. The compounds of this invention inhibit binding of toxins, such as heat-labile enterotoxin (LT) or cholera toxin (CT), to their receptors either in vitro or in vivo. Additionally, the compounds of this invention inhibit binding enterovirulent organisms (e.g., bacteria, virus, fungi, and the like) such as *Vibrio cholerae* and enterotoxigenic strains of *Escherichia coli*, to their cell surface receptors.

References

The following publications, patents and patent applications are cited in this application as superscript numbers:

[1] Spangler, B. D., "Structure and Function of Cholera Toxin and Related *Escherichia coli* Heat-Labile Enterotoxin", Microbiological Reviews, 56(4): 622–647 (1992).
[2] Hol, W. G. J., et al., "Structure and Function of *E. coli* Heat-Labile Enterotoxin and Cholera Toxin B Pentamer", Bacterial Toxins and Virulence Factors in Disease, Ed. by J. Moss et al., Marcel Dekker, Inc. (1995).
[3] Williams (ed.), Synthesis of Optically Active α-Amino Acids, Pergamon Press (1989).
[4] Evans et al., J. Amer. Chem. Soc., 112: 4011–4030 (1990).
[5] Pu et al., J. Amer. Chem. Soc., 56: 1280–1283 (1991).
[6] Williams et al., J. Amer. Chem. Soc., 113: 9276–9286 (1991).
[7] Maarten H. D. Postema, "Recent Developments in the Synthesis of C- Glycosides" Tetrahedron, Vol. 48, No. 40, pp. 8545–8599 (1992).
[8] O. R. Martin et al., J. Org. Chem. 1990, 55, 5188–5190.
[9] L. Petrus et al., Chem zvesti 1982, 36, 103.
[10] A. Förtsch et al., Carbohydr. Res. 1987, 164, 391.
[11] Y. Araki et al., Tetrahedron Lett. 1987, 28, 5853.
[12] B. Giese et al., Angew. Chem. Intl. Ed. Engl. 1986, 25, 450.
[13] Norberg et al., Carbohydr. Res. 1988, 183, 71.
[14] R. M. Williams et al., Tetrahedron Lett. 1983, 27, 2715.
[15] A. O. Stewart et al., J. Am. Chem. Soc. 1985, 107, 4289.
[16] D. S. Brown et al., Tetrahedron Lett. 1989, 45, 4293.
[17] K. Narasaka et al., Chem. Lett. 1987, 2139.
[18] S. Murata et al., Tetrahedron Lett. 1982, 25, 2601.
[19] T. Mukaiyama et al., Carbohydr. Res. 1987, 171, 71.
[20] M. Shimizu et al., Chem. Lett. 1984, 1531.
[21] M. G. Hoffman et al., Liebigs Ann. Chem. 1985, 2403.
[22] P. Allevi et al., J. Chem. Soc., Chem. Commun. 1987, 101.
[23] Kagen et al., Synlett, 1990, 643–650.
[24] U.S. Pat. No. 5,580,858, issued December 3, 1996, to R. M. Ippolito et al.
[25] M. Dubois et al., Anal. Chem., 28, (1979) 350–356.
[26] U.S. Pat. No. 4,137,401, issued January 30, 1979, to R. Lemieux et al.
[27] H. H. Westal et al., "Methods of Enzymology," 34(b), 64 (1974).
[28] Svennerholm, A-M. et al., Current Microbiology, 1: 19–23 (1978).

All of the above publications, patents and patent applications are herein incorporated by reference in their entirety to the same extent as if each individual publication, patent or patent application was specifically and individually indicated to be incorporated by reference in its entirety.

2. State of the Art

Toxins produced by organisms, such as bacteria, viruses, protozoa, fungi and other organisms, are known to cause a number of animal and human diseases, including many diarrheal diseases. For example, heat-labile enterotoxin ("LT"), secreted by certain enterotoxigenic strains of *Escherichia coli*, has been identified as one of the causative agents of bacterial-induced traveller's diarrhea.[1] Additionally, cholera toxin ("CT"), produced by *Vibrio cholerae*, has been identified as the causative agent of the severe diarrheal disease, cholera.[1]

Heat-labile enterotoxin and cholera toxin are known to bind to oligosaccharide receptors on host cells as an initial step in the pathological development of the associated disease condition.[2] Specifically, both LT and CT are known to bind to ganglioside $G_{M1}$, a glycosphingolipid situated in the outer leaflet of the host cell membrane.[2] $G_{M1}$ has a characteristic pentasaccharide structure, i.e., Gal(β1→3)GalNAc(β1→4){NeuAc(α2→3)}Gal(β1-→4)Glc, on its surface which serves as a receptor for LT and CT. LT is also known to bind to other gangliosides, such as ganglioside $G_{D1b}$.

Additionally, many virulent organisms (e.g., bacteria, virus, fungi, and the like) including enterovirulent organisms bind to cell surface receptors as part of the disease process. For example, bacteria such as *Vibrio cholerae* and enterotoxigenic strains of *Escherichia coli* can directly bind to cell surface receptors forming a colony at the point of attachment. Such binding is detrimental because it permits expressed toxin to immediately interact with the cell surface.

In order to ameliorate or prevent the noxious or deleterious effects caused by toxins and organisms, it would be highly desirable to be able to inhibit the binding of the toxin or the organism to its corresponding cell surface receptor. The present invention provides novel 1-galactose derivatives which effectively inhibit such binding.

SUMMARY OF THE INVENTION

This invention is directed to the discovery of a novel class of 1-galactose derivatives which inhibit the binding of toxins, such as heat-labile enterotoxin (LT) or cholera toxin (CT), to their receptors. The compounds of this invention also inhibit binding of organisms, such as *Vibrio cholerae* and enterotoxigenic strains of *Escherichia coli*, to their cell surface receptors.

Accordingly, in one of its composition aspects, this invention provides compounds of formula I:

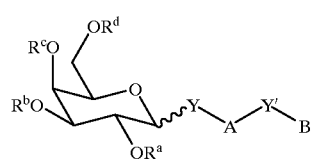

I wherein

A is selected from the group consisting of arylene, cycloalkylene, cycloalkenylene, heteroarylene and divalent heterocyclic;

B is selected from the group consisting of cycloalkyl, cycloalkenyl and heterocyclic;

Y is selected from the group consisting of alkylene, substituted alkylene and —N(R¹)—, wherein R¹ is selected from the group consisting of —C(O)R² and —SO₂R³, wherein R² and R³ are independently selected from the group consisting of alkyl, alkenyl, alkaryl, alkoxyalkyl, aryl, cycloalkyl, cycloalkenyl, heteroaryl, heterocyclic and thioalkoxyalkyl;

Y' is selected from the group consisting of oxygen, sulfur, —S(O)—, —SO₂—, alkylene, substituted alkylene, and —N(R⁴)—, wherein R⁴ is selected from the group consisting of hydrogen, alkyl, alkenyl, alkaryl, alkoxyalkyl, aryl, cycloalkyl, cycloalkenyl, heteroaryl, heterocyclic, thioalkoxyalkyl, —C(O)R⁵ and —SO₂R⁶, wherein $R^5$ and $R^6$ are independently selected from the group consisting of alkyl, alkenyl, alkaryl, alkoxyalkyl, aryl, cycloalkyl, cycloalkenyl, heteroaryl, heterocyclic and thioalkoxyalkyl; and $R^a$, $R^b$, $R^c$ and $R^d$ are each independently selected from the group consisting of hydrogen; sulfate; —C(O)$R^7$, wherein $R^7$ is selected from the group consisting of alkyl, alkenyl, alkaryl, alkoxyalkyl, aryl, cycloalkyl, cycloalkenyl, heteroaryl, heterocyclic and thioalkoxyalkyl; and —P(O)(O$R^8$)$_2$, wherein each $R^8$ is independently selected from the group consisting of hydrogen, alkyl, alkenyl, alkaryl, alkoxyalkyl, aryl, cycloalkyl, cycloalkenyl, heteroaryl, heterocyclic and thioalkoxyalkyl;

and pharmaceutically acceptable salts thereof.

In one preferred embodiment, the present invention is directed to the α-anomers of compounds of formula I. In another preferred embodiment, this invention is directed to the β-anomers of compounds of formula I.

In formula I above, A is preferably a cycloalkylene group having from 5 to 7 carbon atoms. More preferably, A is a cycloalkylene group having from 5 to 7 carbon atom wherein the cycloalkylene group is substituted with 1 to 3 alkyl groups. Still more preferably, A is a cyclopentylene, methylcyclopentylene, dimethylcyclopentylene, cyclohexylene, methylhexylene, dimethylcyclohexylene or cycloheptylene group. Still more preferably, A is a dimethylcyclopentylene group.

Preferably, B is a cycloalkyl group having from 4 to 7 carbon atoms. More preferably, B is a cycloalkyl group having 4 to 7 carbon atoms wherein the cycloalkyl group is substituted with 1 to 3 alkyl groups. More preferably, B is a cyclobutyl, methylcyclobutyl, dimethylcyclobutyl, cyclopentyl, methylcyclopentyl, dimethylcyclopentyl, cyclohexyl, dimethylcyclohexyl or cycloheptyl group. Still more preferably, B is a cyclobutyl or dimethylcyclobutyl group.

In one preferred embodiment of this invention, Y is alkylene or substituted alkylene. Preferably, Y is alkylene of from 1 to 6 carbon atoms. More preferably, Y is a methylene group.

In another preferred embodiment, Y is —N($R^1$)—. Preferably, $R^1$ is —C(O)$R^2$, where $R^2$ is alkyl of from 1 to about 6 carbon atoms. More preferably, $R^2$ is methyl (i.e., Y is —N(COCH$_3$)—).

Preferably, Y' is —NH—.

Preferably, $R^a$, $R^b$, $R^c$ and $R^d$ are each independently selected from the group consisting of hydrogen and —C(O)$R^7$, where $R^7$ is alkyl. More preferably, $R^a$, $R^b$, $R^c$ and $R^d$ are each hydrogen.

In another of its composition aspects, this invention provides a pharmaceutical composition comprising from 1 to 99 weight percent of a pharmaceutically acceptable carrier and from 1 to 99 weight percent of at least one compound of formula I above.

In one of its method aspects, this invention is directed to a method of ameliorating conditions associated with binding of a toxin to its receptor in an animal which method comprises administering to said animal an effective amount of a pharmaceutical composition comprising from 1 to 99 weight percent of a pharmaceutically acceptable carrier and from 1 to 99 weight percent of at least one compound of formula I above, wherein the compound of formula I inhibits the binding of the toxin to its receptor.

In preferred embodiments of this invention, the toxin in the above method is heat-labile enterotoxin or cholera toxin.

In another of its method aspects, this invention is directed to a method of ameliorating conditions associated with binding of an organism to its cell surface receptor in an animal which method comprises administering to said animal an effective amount of a pharmaceutical composition comprising from 1 to 99 weight percent of a pharmaceutically acceptable carrier and from 1 to 99 weight percent of at least one compound of formula I above, wherein the compound of formula I inhibits the binding of the organism to its cell surface receptor.

In preferred embodiments of this invention, the organism in the above method is *Vibrio cholerae* or an enterotoxigenic strain of *Escherichia coli*.

This invention is also directed to 1-galactose derivative-containing supports which are useful for inhibiting the binding of a toxin to its receptor. Supports useful for inhibiting the binding of an organism to its cell surface receptor are also provided.

Accordingly, in yet another of its composition aspects, this invention provides a 1-galactose derivative-containing support comprising a support having covalently bound thereto a plurality of at least one compound of formula I':

I' wherein

A is selected from the group consisting of arylene, cycloalkylene, cycloalkenylene, heteroarylene and divalent heterocyclic;

B is selected from the group consisting of cycloalkyl, cycloalkenyl and heterocyclic;

Y is selected from the group consisting of alkylene, substituted alkylene and —N($R^1$)—, wherein $R^1$ is selected from the group consisting of —C(O)$R^2$ and —SO$_2$$R^3$, wherein $R^2$ and $R^3$ are independently selected from the group consisting of alkyl, alkenyl, alkaryl, alkoxyalkyl, aryl, cycloalkyl, cycloalkenyl, heteroaryl, heterocyclic and thioalkoxyalkyl;

Y' is selected from the group consisting of oxygen, sulfur, —S(O)—, —SO$_2$—, alkylene, substituted alkylene, and —N($R^4$)—, wherein $R^4$ is selected from the group consisting of hydrogen, alkyl, alkenyl, alkaryl, alkoxyalkyl, aryl, cycloalkyl, cycloalkenyl, heteroaryl, heterocyclic, thioalkoxyalkyl, —C(O)$R^5$ and —SO$_2$$R^6$, wherein $R^5$ and $R^6$ are independently selected from the group consisting of alkyl, alkenyl, alkaryl, alkoxyalkyl, aryl, cycloalkyl, cycloalkenyl, heteroaryl, heterocyclic and thioalkoxyalkyl; and $R^a$, $R^b$, $R^c$ and $R^d$ are each independently selected from the group consisting of hydrogen; sulfate; —C(O)$R^7$, wherein $R^7$ is selected from the group consisting of alkyl, alkenyl, alkaryl, alkoxyalkyl, aryl, cycloalkyl, cycloalkenyl, heteroaryl, heterocyclic and thioalkoxyalkyl; and —P(O)(O$R^8$)$_2$, wherein each $R^8$ is independently selected from the group consisting of hydrogen, alkyl, alkenyl, alkaryl, alkoxyalkyl, aryl, cycloalkyl, cycloalkenyl, heteroaryl, heterocyclic and thioalkoxyalkyl;

and pharmaceutically acceptable salts thereof;

wherein one of A, B, $R^a$, $R^b$, $R^c$ or $R^d$ is covalently bound via a linking arm to the support.

In still another of its composition aspects, this invention provides a pharmaceutical composition comprising from 1 to 99 weight percent of a pharmaceutically acceptable carrier and from 1 to 99 weight percent of a 1-galactose derivative-containing support comprising a support having covalently bound thereto a plurality of at least one compound of formula I'.

In another of its method aspects, this invention is directed to a method of ameliorating conditions associated with binding of a toxin to its receptor in an animal which method comprises administering to said animal an effective amount of a pharmaceutical composition comprising from 1 to 99 weight percent of a pharmaceutically acceptable carrier and from 1 to 99 weight percent of a 1-galactose derivative-containing support comprising a support having covalently bound thereto a plurality of at least one compound of formula I', wherein the compound of formula I' inhibits the binding of the toxin to its receptor.

In another of its method aspects, this invention is directed to a method of ameliorating conditions associated with binding of an organism to its cell surface receptor in an animal which method comprises administering to said animal an effective amount of a pharmaceutical composition comprising from 1 to 99 weight percent of a pharmaceutically acceptable carrier and from 1 to 99 weight percent of a 1-galactose derivative-containing support comprising a support having covalently bound thereto a plurality of at least one compound of formula I', wherein the compound of formula I' inhibits the binding of the organism to its cell surface receptor.

In a preferred embodiment of this invention, the support employed in the above compositions and methods is a non-absorbable support. More preferably, the support is a non-absorbable solid support.

Preferred compounds of formula I above for use in this invention include those et forth in formula IA below:

IA wherein A, B, Y, and Y' are selected as shown in Table I below.

TABLE I

| Y | A | Y' | B |
|---|---|----|---|
| —CH$_2$— | 2,2-dimethylcyclopent-1,4-diyl | —NH— | cyclobut-1-yl |
| —CH$_2$— | 2,2-dimethylcyclopent-1,4-diyl | —NH— | 3,3-dimethylcyclobut-1-yl |
| —CH$_2$— | 2,2-dimethylcyclopent-1,4-diyl | —NH— | cyclopent-1-yl |
| —CH$_2$— | 2,2-dimethylcyclopent-1,4-diyl | —NH— | 3-methylcyclopent-1-yl |
| —CH$_2$— | 2,2-dimethylcyclopent-1,4-diyl | —NH— | 3,3-dimethycyclopent-1-yl |
| —CH$_2$— | 2,2-dimethylcyclopent-1,4-diyl | —NH— | cyclohex-1-yl |
| —CH$_2$— | 2,2-dimethylcyclopent-1,4-diyl | —NH— | 3-methylcyclohex-1-yl |
| —CH$_2$— | 2,2-dimethylcyclopent-1,4-diyl | —NH— | 4-methylcyclohex-1-yl |
| —CH$_2$— | 2,2-dimethylcyclopent-1,4-diyl | —O— | cyclobut-1-yl |
| —CH$_2$— | 2,2-dimethylcyclopent-1,4-diyl | —O— | 3,3-dimethylcyclobut-1-yl |

TABLE I-continued

| Y | A | Y' | B |
|---|---|----|---|
| —CH$_2$— | 2,2-dimethylcyclopent-1,4-diyl | —O— | cyclopent-1-yl |
| —CH$_2$— | 2,2-dimethylcyclopent-1,4-diyl | —O— | 3-methylcyclopent-1-yl |
| —CH$_2$— | 2,2-dimethylcyclopent-1,4-diyl | —O— | 3,3-dimethycyclopent-1-yl |
| —CH$_2$— | 2,2-dimethylcyclopent-1,4-diyl | —O— | cyclohex-1-yl |
| —CH$_2$— | 2,2-dimethylcyclopent-1,4-diyl | —O— | 3-methylcyclohex-1-yl |
| —CH$_2$— | 2,2-dimethylcyclopent-1,4-diyl | —O— | 4-methylcyclohex-1-yl |
| —CH$_2$— | 2,2-dimethylcyclopent-1,4-diyl | —S— | cyclobut-1-yl |
| —CH$_2$— | 2,2-dimethylcyclopent-1,4-diyl | —S— | 3,3-dimethylcyclobut-1-yl |
| —CH$_2$— | 2,2-dimethylcyclopent-1,4-diyl | —S— | cyclopent-1-yl |
| —CH$_2$— | 2,2-dimethylcyclopent-1,4-diyl | —S— | 3-methylcyclopent-1-yl |
| —CH$_2$— | 2,2-dimethylcyclopent-1,4-diyl | —S— | 3,3-dimethycyclopent-1-yl |
| —CH$_2$— | 2,2-dimethylcyclopent-1,4-diyl | —S— | cyclohex-1-yl |
| —CH$_2$— | 2,2-dimethylcyclopent-1,4-diyl | —S— | 3-methylcyclohex-1-yl |
| —CH$_2$— | 2,2-dimethylcyclopent-1,4-diyl | —S— | 4-methylcyclohex-1-yl |
| —NAc—[1] | 2,2-dimethylcyclopent-1,4-diyl | —NH— | cyclobut-1-yl |
| —NAc— | 2,2-dimethylcyclopent-1,4-diyl | —NH— | 3,3-dimethylcyclobut-1-yl |
| —NAc— | 2,2-dimethylcyclopent-1,4-diyl | —NH— | cyclopent-1-yl |
| —NAc— | 2,2-dimethylcyclopent-1,4-diyl | —NH— | 3-methylcyclopent-1-yl |
| —NAc— | 2,2-dimethylcyclopent-1,4-diyl | —NH— | 3,3-dimethycyclopent-1-yl |
| —NAc— | 2,2-dimethylcyclopent-1,4-diyl | —NH— | cyclohex-1-yl |
| —NAc— | 2,2-dimethylcyclopent-1,4-diyl | —NH— | 3-methylcyclohex-1-yl |
| —NAc— | 2,2-dimethylcyclopent-1,4-diyl | —NH— | 4-methylcyclohex-1-yl |
| —NAc— | 2,2-dimethylcyclopent-1,4-diyl | —O— | cyclobut-1-yl |
| —NAc— | 2,2-dimethylcyclopent-1,4-diyl | —O— | 3,3-dimethylcyclobut-1-yl |
| —NAc— | 2,2-dimethylcyclopent-1,4-diyl | —O— | cyclopent-1-yl |
| —NAc— | 2,2-dimethylcyclopent-1,4-diyl | —O— | 3-methylcyclopent-1-yl |
| —NAc— | 2,2-dimethylcyclopent-1,4-diyl | —O— | 3,3-dimethycyclopent-1-yl |
| —NAc— | 2,2-dimethylcyclopent-1,4-diyl | —O— | cyclohex-1-yl |
| —NAc— | 2,2-dimethylcyclopent-1,4-diyl | —O— | 3-methylcyclohex-1-yl |
| —NAc— | 2,2-dimethylcyclopent-1,4-diyl | —O— | 4-methylcyclohex-1-yl |
| —NAc— | 2,2-dimethylcyclopent-1,4-diyl | —S— | cyclobut-1-yl |
| —NAc— | 2,2-dimethylcyclopent-1,4-diyl | —S— | 3,3-dimethylcyclobut-1-yl |
| —NAc— | 2,2-dimethylcyclopent-1,4-diyl | —S— | cyclopent-1-yl |
| —NAc— | 2,2-dimethylcyclopent-1,4-diyl | —S— | 3 -methylcyclopent-1-yl |
| —NAc— | 2,2-dimethylcyclopent-1,4-diyl | —S— | 3,3-dimethycyclopent-1-yl |
| —NAc— | 2,2-dimethylcyclopent-1,4-diyl | —S— | cyclohex-1-yl |
| —NAc— | 2,2-dimethylcyclopent-1,4-diyl | —S— | 3-methylcyclohex-1-yl |

TABLE I-continued

| Y | A | Y' | B |
|---|---|---|---|
| —NAc— | 2,2-dimethylcyclopent-1,4-diyl | —S— | 4-methylcyclohex-1-yl |

[1]Ac = acetyl = —C(O)CH$_3$

DETAILED DESCRIPTION OF THE INVENTION

Figure 1:
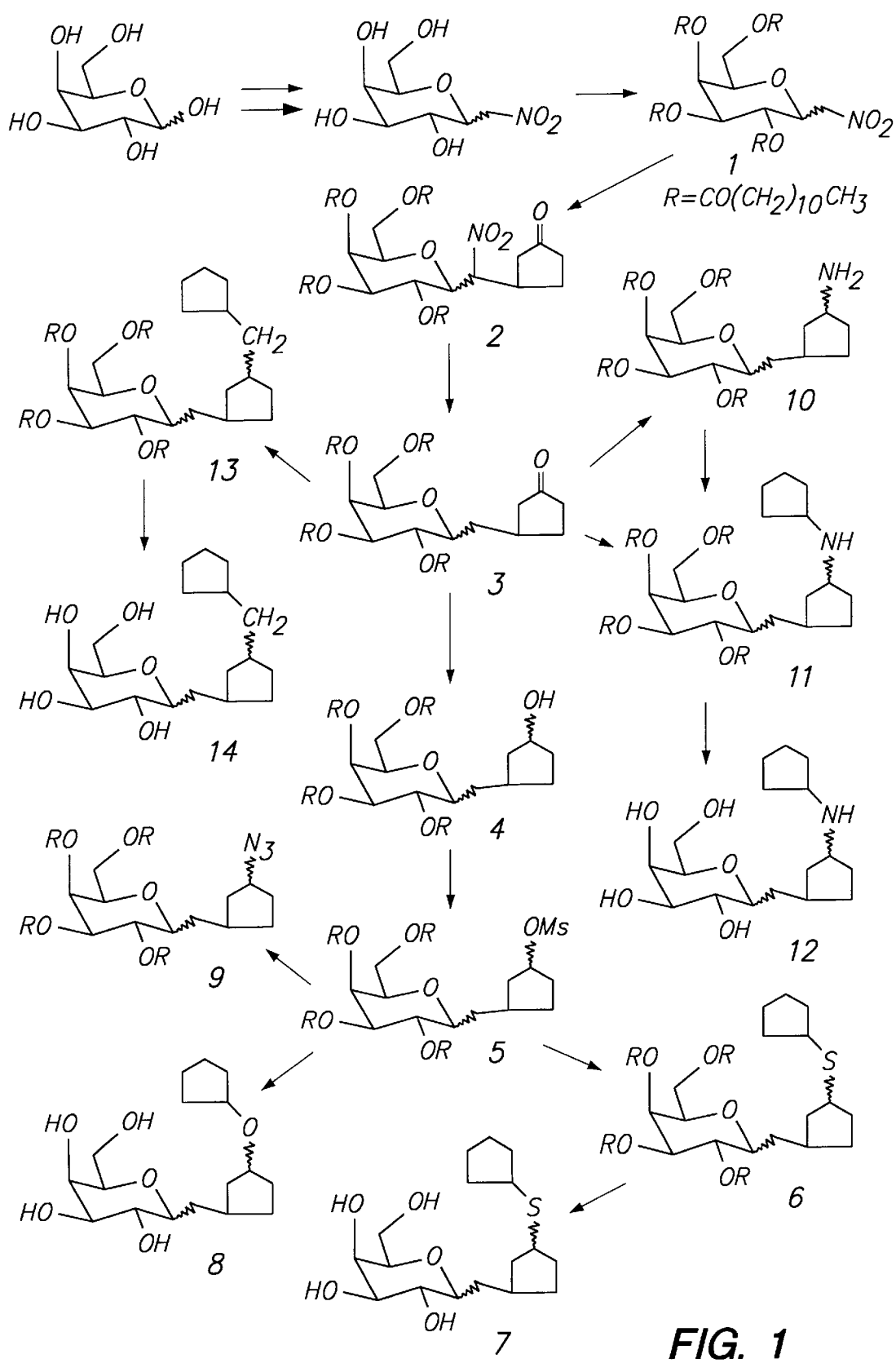
FIG. 1 illustrates a preferred reaction scheme which can be used to prepare various 1-galactose derivatives having a carbon-containing aglycon linking group.

This invention relates, in one embodiment, to compounds which inhibit the binding of a toxin, such as heat-labile enterotoxin or cholera toxin, to its receptor either in vitro or in vivo. In another embodiment, the compounds of this invention inhibit binding of an organism (e.g., bacteria, virus, fungi, and the like), such as *Vibrio cholerae* or enterotoxigenic strains of *Escherichia coli*, to its cell surface receptor. When describing the compounds of this invention, the following terms have the following meanings, unless otherwise indicated.

Definitions

"Acyl" refers to the groups alkyl—C(O)—, aryl—C(O)—, and heteroaryl—C(O)— where alkyl, aryl and heteroaryl are as defined herein.

"Acylamino" refers to the group —C(O)NRR where each R is independently hydrogen or alkyl.

"Acyloxy" refers to the groups alkyl—C(O)O—, aryl—C(O)O—, heteroaryl—C(O)O—, and heterocyclic—C(O)O— where alkyl, aryl, heteroaryl and heterocyclic are as defined herein.

"Alkaryl" refers to -alkylene-aryl groups preferably having from 1 to 8 carbon atoms in the alkylene moiety and from 6 to 10 carbon atoms in the aryl moiety. Such alkaryl groups are exemplified by benzyl, phenethyl and the like.

"Alkoxy" refers to the group alkyl—O—. Such alkoxy groups include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Alkoxyalkyl" refers to the group -alkylene—O—alkyl which includes by way of example, methoxymethyl (CH$_3$OCH$_2$—), methoxyethyl (CH$_3$—O—CH$_2$CH$_2$—) and the like.

"Alkenyl" refers to alkenyl groups preferably having from 2 to 8 carbon atoms and more preferably 2 to 6 carbon atoms and having at least 1 and preferably from 1–2 sites of alkenyl unsaturation. Such alkenyl groups include ethenyl (—CH=CH$_2$), n-propenyl (i.e., allyl) (—CH$_2$CH=CH$_2$), iso-propenyl (—C(CH$_3$)=CH$_2$), and the like.

"Alkyl" refers to monovalent alkyl groups preferably having from 1 to 8 carbon atoms and more preferably 1 to 6 carbon atoms. This term is exemplified by groups such as methyl, ethyl, n-propyl, iso-propyl, n-butyl, iso-butyl, n-hexyl, and the like.

"Substituted alkyl" refers to a branched or straight chain alkyl group of from 1 to 8 carbon atoms having from 1 to 3 substituents selected from the group consisting of hydroxy, acyl, acylamino, acyloxy, alkoxy, alkenyl, alkynyl, amino, aminoacyl, aryl, aryloxy, carboxy, carboxyalkyl, cyano, cycloalkyl, guanidino, halo, heteroaryl, heterocyclic, nitro, thiol, thioaryloxy, thioheteroaryloxy, and the like. Preferred substituents include hydroxy and amino.

"Alkylene" or "alkyldiyl" refers to divalent alkylene groups preferably having from 1 to 8 carbon atoms and more preferably 1 to 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Substituted alkylene" or "substituted alkyldiyl" refers to divalent alkylene groups of from 1 to 8 carbon atoms having from 1 to 3 substituents selected from the group consisting of hydroxy, acyl, acylamino, acyloxy, alkoxy, alkenyl, alkynyl, amino, aminoacyl, aryl, aryloxy, carboxy, carboxyalkyl, cyano, cycloalkyl, guanidino, halo, heteroaryl, heterocyclic, nitro, thiol, thioaryloxy, thioheteroaryloxy, and the like. Preferred substituents include alkyl, hydroxy and amino.

"Alkynyl" refers to alkynyl groups preferably having from 2 to 8 carbon atoms and more preferably 2 to 6 carbon atoms and having at least 1 and preferably from 1–2 sites of alkynyl unsaturation. Such alkynyl groups include ethynyl (—C≡CH), propargyl (—CH$_2$C≡CH) and the like.

"Amino acid" refers to any of the naturally occurring amino acids, as well as synthetic analogs and derivatives thereof. α-Amino acids comprise a carbon atom to which is bonded an amino group, a carboxy group, a hydrogen atom, and a distinctive group referred to as a "side chain". The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), alkaryl (e.g., as in phenylalanine and tryptophan), substituted arylalkyl (e.g., as in tyrosine), and heteroarylalkyl (e.g., as in histidine).

One of skill in the art will appreciate that the term "amino acid" can also include β-, γ-, δ-, and ω-amino acids, and the like. Unnatural amino acids are also known in the art, as set forth in, for example, Williams[3], Evans et al.[4], Pu et al.[5], Williams et al.[6], and all references cited therein. Stereoisomers (e.g., D-amino acids) of the twenty conventional amino acids, unnatural amino acids such as α,α-disubstituted amino acids and other unconventional amino acids may also be suitable components for compounds of the present invention. Examples of unconventional amino acids include: 4-hydroxyproline, 3-methylhistidine, 5-hydroxylysine, and other similar amino acids and imino acids (e.g., 4-hydroxyproline).

"Aminoacyl" refers to the group —NRC(O)R where each R is independently hydrogen or alkyl.

"Aryl" refers to an unsaturated aromatic carbocyclic group of from 6 to 14 carbon atoms having a single ring (e.g., phenyl) or multiple condensed rings (e.g., naphthyl or anthryl). Preferred aryls include phenyl, naphthyl and the like.

Unless otherwise constrained by the definition for the aryl substituent, such aryl groups can optionally be substituted with from 1 to 3 substituents selected from the group consisting of hydroxy, acyl, acyloxy, alkyl, substituted alkyl, alkoxy, alkenyl, alkynyl, amino, aminoacyl, aryl, aryloxy, carboxy, carboxyalkyl, cyano, halo, nitro, heteroaryl, trihalomethyl and the like. Preferred substituents include alkyl, alkoxy, halo, carboxy, cyano, nitro, trihalomethyl, and thioalkoxy.

"Arylene" refers to a divalent unsaturated aromatic carbocyclic group of from 6 to 14 carbon atoms having a single ring (e.g., phenyl) or multiple condensed rings (e.g., naphthyl or anthryl). Preferred arylenes include phenyl, naphthyl and the like.

Unless otherwise constrained by the definition for the arylene substituent, such arylene groups can optionally be substituted with from 1 to 3 substituents selected from the group consisting of hydroxy, acyl, acyloxy, alkyl, substituted alkyl, alkoxy, alkenyl, alkynyl, amino, aminoacyl, aryl, aryloxy, carboxy, carboxyalkyl, cyano, halo, nitro, heteroaryl, trihalomethyl and the like. Preferred substituents include alkyl, alkoxy, halo, carboxy, cyano, nitro, trihalomethyl, and thioalkoxy.

"Aryloxy" refers to the group aryl—O— where the aryl group is as defined herein including optionally substituted aryl groups as also defined herein.

"Carboxy" refers to the group —COOH.

"Carboxyalkyl" refers to the group —C(O)O—alkyl where alkyl is as defined herein.

"Cycloalkyl" refers to cyclic alkyl groups of from 3 to 20 carbon atoms, preferably 4 to 8 carbon atoms, having a single cyclic ring or multiple condensed rings which can be optionally substituted with from 1 to 3 substituents selected from the group consisting of hydroxy, acyl, acyloxy, alkyl, substituted alkyl, alkylene, alkoxy, alkenyl, alkynyl, amino, aminoacyl, aryl, aryloxy, carboxy, carboxyalkyl, cyano, halo, nitro, heteroaryl, trihalomethyl and the like. Preferred substituents include alkyl, alkoxy, halo, carboxy, cyano, nitro, trihalomethyl, and thioalkoxy. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures such as adamantanyl and the like, and spiro compounds. Examples of suitable cycloalkyl rings include single ring structures such as cyclopentane, cyclohexane, cycloheptane, cyclooctane, and the like, or multiple ring structures such as bicyclo[2.2.1]heptane, bicyclo[3.2.1]octane, and the like. Preferred cycloalkyl rings include cyclopentane, cyclohexane, cycloheptane and bicyclo[3.2.1]octane.

"Cycloalkylene" or "cycloalkyldiyl" refers to a divalent cyclic alkylene group of from 3 to 20 carbon atoms, preferably 4 to 8 carbon atoms, having a single cyclic ring or multiple condensed rings which can be optionally substituted with from 1 to 3 substituents selected from the group consisting of hydroxy, acyl, acyloxy, alkyl, substituted alkyl, alkylene, alkoxy, alkenyl, alkynyl, amino, aminoacyl, aryl, aryloxy, carboxy, carboxyalkyl, cyano, halo, nitro, heteroaryl, trihalomethyl and the like. Preferred substituents include alkyl, alkoxy, halo, carboxy, cyano, nitro, trihalomethyl, and thioalkoxy. Such cycloalkylene groups include, by way of example, single ring structures such as cyclopropylene, cyclobutylene, cyclopentylene (e.g., cyclopent-1,3-diyl), cyclooctylene, 1-methylcyclopropylene, 2-methylcyclopentylene, 2-methylcyclooctylene, and the like, or multiple ring structures such as adamantanylene, and the like.

"Cycloalkenyl" refers to cyclic alkenyl groups of from 4 to 20 carbon atoms, preferably 5 to 8 carbon atoms, having a single cyclic ring and at least one point of internal unsaturation. Optionally, such cycloalkenyl groups can be substituted with from 1 to 3 substituents selected from the group consisting of hydroxy, acyl, acyloxy, alkyl, substituted alkyl, alkylene, alkoxy, alkenyl, alkynyl, amino, aminoacyl, aryl, aryloxy, carboxy, carboxyalkyl, cyano, halo, nitro, heteroaryl, trihalomethyl and the like. Preferred substituents include alkyl, alkoxy, halo, carboxy, cyano, nitro, trihalomethyl, and thioalkoxy. Examples of cycloalkenyl groups include, cyclopentenyl, cyclohexenyl, and the like.

"Cycloalkenylene" or "cycloalkenyldiyl" refers to cyclic alkenylene groups of from 4 to 20 carbon atoms, preferably 5 to 8 carbon atoms, having a single cyclic ring and at least one point of internal unsaturation. Optionally, such cycloalkenylene groups can be substituted with from 1 to 3 substituents selected from the group consisting of hydroxy, acyl, acyloxy, alkyl, substituted alkyl, alkylene, alkoxy, alkenyl, alkynyl, amino, aminoacyl, aryl, aryloxy, carboxy, carboxyalkyl, cyano, halo, nitro, heteroaryl, trihalomethyl and the like. Preferred substituents include alkyl, alkoxy, halo, carboxy, cyano, nitro, trihalomethyl, and thioaikoxy. Examples of cycloalkenylene groups include, for instance, cyclopentenylene, cyclohexenylene, and the like.

"Halo" or "halogen" refers to fluoro, chloro, bromo and iodo and preferably is either chloro or bromo.

"Heteroaryl" refers to a monovalent aromatic group of from 2 to 8 carbon atoms and 1 to 4 heteroatoms selected from oxygen, nitrogen and sulfur within the ring.

Unless otherwise constrained by the definition for the heteroaryl substituent, such heteroaryl groups can be optionally substituted with 1 to 3 substituents selected from the group consisting of alkyl, substituted alkyl, alkoxy, aryl, aryloxy, halo, nitro, heteroaryl, thioalkoxy, thioaryloxy and the like. Such heteroaryl groups can have a single ring (e.g., pyridyl or furyl) or multiple condensed rings (e.g., indolizinyl or benzothienyl). Preferred heteroaryls include pyridyl, pyrrolyl and furyl.

"Heteroarylene" refers to a divalent aromatic group of from 2 to 8 carbon atoms and 1 to 4 heteroatoms selected from oxygen, nitrogen and sulfur within the ring.

Unless otherwise constrained by the definition for the heteroarylene substituent, such heteroarylene groups can be optionally substituted with 1 to 3 substituents selected from the group consisting of alkyl, substituted alkyl, alkoxy, aryl, aryloxy, halo, nitro, heteroaryl, thioalkoxy, thioaryloxy and the like. Such heteroarylene groups can have a single ring (e.g., pyridylene or furylene) or multiple condensed rings (e.g., indolizinylene or benzothienylene). Preferred heteroarylenes include pyridylene, pyrrolylene and furylene.

"Heterocycle" or "heterocyclic" refers to a monovalent saturated or unsaturated group having a single ring or multiple condensed rings, of from 1 to 8 carbon atoms and from 1 to 4 hetero atoms selected from nitrogen, sulfur or oxygen within the ring. For the purposes of this application, the term "heterocycle" or "heterocyclic" does not include carbohydrate rings (i.e. mono- or oligosaccharides).

Unless otherwise constrained by the definition for the heterocyclic substituent, such heterocyclic groups can be optionally substituted with 1 to 3 substituents selected from the group consisting of alkyl, substituted alkyl, alkylene, alkoxy, aryl, aryloxy, halo, nitro, heteroaryl, thioalkoxy, thioaryloxy and the like. Such heterocyclic groups can have a single ring (e.g., pyrrolidinyl, piperidinyl, morpholinyl or tetrahydrofuranyl) or multiple condensed rings (e.g., indolinyl).

"Heterocyclene" or "divalent heterocyclic" refers to a divalent saturated or unsaturated group having a single ring or multiple condensed rings, of from 1 to 8 carbon atoms and from 1 to 4 hetero atoms selected from nitrogen, sulfur or oxygen within the ring. For the purposes of this application, the term "heterocyclene" or "divalent heterocyclic" does not include divalent carbohydrate rings (i.e. mono- or oligosaccharides).

Unless otherwise constrained by the definition for the divalent heterocyclic substituent, such divalent heterocyclic groups can be optionally substituted with 1 to 3 substituents selected from the group consisting of alkyl, substituted alkyl, alkylene, alkoxy, aryl, aryloxy, halo, nitro, heteroaryl, thioalkoxy, thioaryloxy and the like. Such divalent heterocyclic groups can have a single ring or multiple condensed rings.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline and the like.

"Thioalkoxyalkyl" refers to the group -alkylene—S—alkyl which includes by way of example, thiomethoxymethyl ($CH_3SCH_2$—), thiomethoxyethyl ($CH_3$—S—$CH_2CH_2$—) and the like.

"Thiol" refers to the group —SH.

"Thioalkoxy" refers to the group —S—alkyl wherein the alkyl group is as defined herein.

"Thioaryloxy" refers to the group aryl—S—wherein the aryl group is as defined herein, including optionally substituted aryl groups as also defined herein.

"Thioheteroaryloxy" refers to the group heteroaryl—S—wherein the heteroaryl group is as defined herein, including optionally substituted heteroaryl groups as also defined herein.

The term "linking arm" refers to a chemical group or covalent bond which optionally covalently attaches the 1-galactose derivative to a support. Such groups typically comprise an alkylene, arylene or alkarylene group and at least one heteroatom, preferably 2 to 6 heteroatoms. A particularly preferred linking arm is illustrated in the formula:

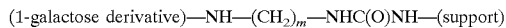

(1-galactose derivative)—NH—$(CH_2)_m$—NHC(O)NH—(support)

wherein m is an integer of from 2 to about 10. Preferably, m is 6.

The term "support" refers to an inert material or molecule to which a 1-galactose derivative may be covalently bound, either directly or through a linking arm. When used in vivo, the solid support will be biocompatible and pharmaceutically acceptable. Preferably, the support is a non-absorbable support, i.e., when administered orally, the support passes unaffected through the gut without being absorbed into the circulatory system and is essentially completely eliminated from the body. More preferably, the support is a non-absorbable solid support. Typically, the support will contain a plurality of attachment sites for the 1-galactose derivative, i.e., the support is an oligovalent or polyvalent carrier. Suitable supports range, by way of illustration, from low molecular weight molecules, such 1,3,5-benzenetricarboxylic acid (trimesic acid), to organic and inorganic polymers, polysaccharides, polypeptides, glasses, silicates or minerals.

The term "solid support" refers to an inert, non-absorbable solid material to which a 1-galactose derivative may be covalently bound, preferably via a linking arm. When used in vivo, the solid support will be biocompatible and pharmaceutically acceptable. Suitable solid supports include, by way of example only, silica, including synthetic silicates, such as porous glass; biogenic silicates, such as diatomaceous earth; hydrogels; silicate-containing minerals, such as kaolinite; synthetic polymers, such as polystyrene, polypropylene, etc.; polysaccharides such as dextrans, celluloses (CMC), alginates, chitins, chitosans and cyclodextrins; and the like.

Preferred solid support materials for use in this invention are silica supports which have been silylaminated with a ω-aminoalkyltrialkoxysilane using conventional procedures. Suitable ω-aminoalkyltrialkoxysilanes include, for example, 3-aminopropyltriethoxysilane, 4-aminobutyltriethoxysilane and the like. A particularly preferred silica for use in such silylamination reactions is silica sold commercially under the tradename Chromosorb P™ by Manville Corp., Denver, Colo.

The term "toxin" refers to a compound produced by an organism which causes or initiates the development of a noxious, poisonous or deleterious effect in a host presented with the toxin. Such deleterious conditions may include fever, nausea, diarrhea, weight loss, neurologic disorders, renal disorders, hemorrhage, and the like. As used herein, the term "toxin" includes bacterial toxins, such as cholera toxin, heat-labile and heat-stable toxins of *E. coli*, toxins A and B of *Clostridium difficile*, aerolysins, hemolysins, and the like; toxins produced by protozoa, such as Giardia; toxins produced by fungi; and the like. Included within this term are exotoxins, i.e., toxins secreted by an organism as an extracellular product, and enterotoxins, i.e., toxins present in the gut of an organism.

The terms "heat-labile enterotoxin" or "LT" refer to an enterotoxin of enterotoxigenic *E. coli* which initiates traveller's diarrhea and related conditions. This toxin has a lectin-like activity.

The term "traveller's diarrhea" refers to diarrhea of sudden onset, often accompanied by abdominal cramps, vomiting and fever that occurs sporadically in traveller's, usually during the first week of a trip. This diarrhea is most commonly caused by enterotoxigenic *E. coli*.

The term "cholera" refers to an acute epidemic infectious disease caused by *Vibrio cholerae*, wherein a soluble toxin elaborated in the intestinal tract by the Vibrio alters the permeability of the mucosa, causing a profuse watery diarrhea, extreme loss of fluid and electrolytes, and a state of dehydration and collapse, but no gross morphologic change in the intestinal mucosa.

The terms "cholera toxin" or "CT" refer to an enterotoxin of *V. cholerae* which initiates cholera and related conditions. This toxin has a lectin-like activity.

The phrase "inhibit(s) the binding of a toxin to its receptor" means that a compound inhibits the binding of a toxin to its receptor by at least 20%. For example, useful binding inhibition assays may measure inhibition of binding to ganglioside $G_{D1b}$ or ganglioside $G_{M1}$, neutralization of cytotoxic activity, or the like. Such binding is reported herein as percent toxin activity remaining so that those compounds which result in about 80% or less toxin activity remaining under the bioassay conditions disclosed herein are deemed to inhibit the binding of a toxin to its receptor.

The phrase "inhibit(s) the binding of heat-labile enterotoxin (LT) and/or cholera toxin (CT) to an LT and/or CT receptor" means that a compound inhibits the binding of LT and/or CT to an LT and/or CT receptor by at least 20%.

The phrase "inhibit(s) the binding of an organism to its cell surface receptor" means that a compound inhibits the binding of an organism, such as a bacterium, a virus, a protozoan, a fungus, and the like, to its cell surface receptor. For example, for organisms such as *Vibro cholera* or enterotoxigenic strains of *E. coli*, a compound is said to inhibit binding of an organism to a cell surface receptor if it reduces binding of a bacterial surface adhesion antigen, such as CFA I pili, by at least 10%.

The term "pharmaceutically acceptable salt" refers to pharmaceutically acceptable salts of a compound of formula I which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

For purpose of this application, all sugars are referenced using conventional three letter nomenclature. All sugars are assumed to be in the D-form unless otherwise noted, except for fucose, which is in the L-form. Further, all sugars are in the pyranose form.

When chiral centers are found in the 1-galactose derivatives of this invention other than the chiral centers of the galactose moiety, this invention encompasses all possible stereoisomers, i.e., enantiomers or diastereomers. For example, when A is a cycloalkylene group, the carbon atoms to which Y and Y' are attached may have an R,R or R,S or S,R or S,S configuration. Similarly, B is a cycloalkyl group, the carbon atom to which Y' are attached may have an R or S configuration.

General Synthetic Procedures

The 1-galactose derivatives of this invention may be prepared by the following general methods and procedures. It should be appreciated that where typical or preferred process conditions (e.g., reaction temperatures, times, mole ratios of reactants, solvents, pressures, etc.) are given, other process conditions may also be used unless otherwise stated. Optimum reaction conditions may vary with the particular reactants or solvents used, but such conditions can be determined by one skilled in the art by routine optimization procedures.

The 1-galactose derivatives of this invention where Y is alkylene or substituted alkylene (e.g., C-glycosides) can be prepared by a variety of synthetic procedures well-known in the art. For example, C-glycosides can be prepared via Wittig reactions, palladium mediated reactions, electrophilic reactions (in which the saccharide functions as the electrophile), nucleophilic reactions (in which the saccharide functions as the nucleophile) and free radical reactions. The formation of C-glycoside using these reactions and others is described by Maarten H. D. Postema in "Recent Developments in the Synthesis of C-Glycosides"[7] and references cited therein.

By way of illustration, C-glycoside intermediates useful for preparing the compounds of the present invention can be readily prepared via the Michael addition of C-glycosyl nitromethane deriviatives to cyclic α,β-unsaturated carbonyl compounds, followed by tin hydride reduction of the nitro group, as shown in Scheme 1.

Scheme 1

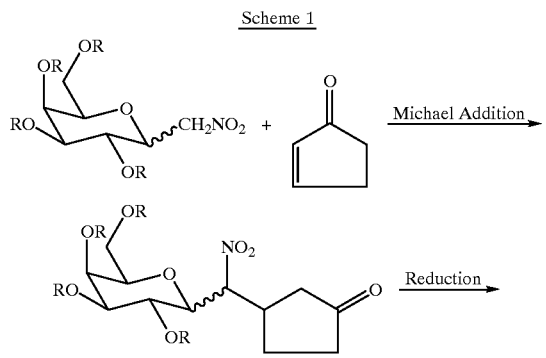

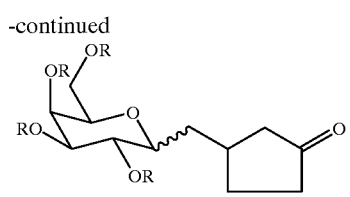

The resulting carbonyl-containing intermediate is then reduced or reductively aminated to give an alcohol or an amine compound. These alcohol or amine compounds are then further reacted via reductive alkylation or by conversion to a leaving group and displacement to afford amines, ethers or thioethers and the like. The carbonyl-containing intermediate can also be reductively aminated to afford amines. Such reactions are well known to those of ordinary skill in the art and can be accomplished using art recognized procedures.

The C-glycosyl nitromethane deriviatives employed in this reaction are readily available in two steps from the parent saccharide. See, for example, O. R. Martin et al.,[8] L. Petrus et al.,[9] A. Förtsch et al.[10] and references cited therein.

Similarly, the cyclic α,β-unsaturated carbonyl compounds suitable for use in preparing the 1-galactose derivatives of this invention are well known in the art. Such compound are either commercially available or can be prepared from commercially available materials using art recognized procedures. Preferred cyclic α,β-unsaturated carbonyl compounds for use in this invention include, by way of example, cyclopent-2-en-1-one, 4,4-dimethylcyclopent-2-en-1-one, cyclohex-2-en-1-one, 4,4-dimethylcyclohex-2-en-1-one, 6,6-dimethylcyclohex-2-en-1-one and cyclohept-en-1-one.

Alternatively, by way of further illustration, free radical addition reactions can be employed to prepare C-glycosides intermediates useful in preparing the compounds of the present invention as shown in Scheme 2.

Scheme 2

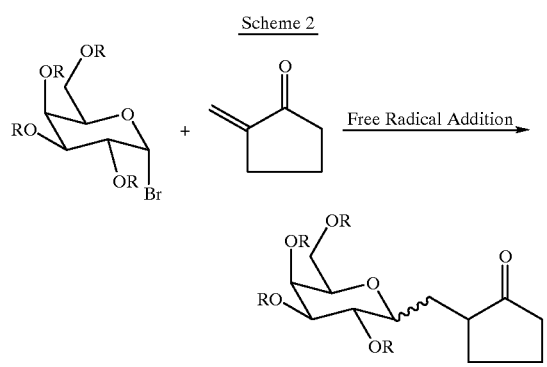

For example, glycosyl bromides have been reacted with α,β-unsaturated ketones as described in Y. Araki et al.[11]; and with a-methylene lactones as described in B. Giese et al.[12] These reactions are typically conducted using tributyltin hydride and 2,2'-azobisisobutyronitrile (AIBN). The resulting carbonyl-containing intermediate is then further derivatized to form alcohols, amines, ethers or thioethers and the like.

The cyclic a-methylene carbonyl compounds used in this reaction are well known in the art. Such compound are either commercially available or can be prepared from commercially available materials using art recognized procedures. Preferred cyclic α-methylene carbonyl compounds for use in this invention include, by way of example, α-methylene cyclopentan-1-one, α-methylene (4,4-dimethyl) cyclopentan-1-one, α-methylene cyclohexan-1-one, α-methylene (4,4-dimethyl)cyclohexan-1-one, α-methylene (6,6-dimethyl)cyclohexan-1-one and α-methylene cycloheptan-1-one.

Similarly, the 1-bromo-D-galactopyranose compounds employed in free radical addition reactions can be prepared using conventional procedures and reagents. For example, treatment of benzyl 2,3,4,6-tetra—O—acylated-α-thiogalactopyranosides (prepared by contacting the peracylated galactopyranoside with about 1 equivalent of benzyl mercaptan (PhCH$_2$SH) and from about 1 to about 3, preferably 2, equivalents of boron trifluoride etherate in dichloromethane) are readily converted into 1-bromo-2,3,4,6-tetra—O—acylated-β-galactopyranosides using bromine and tetraethylammonium bromide using the procedure described, for example, in Norberg et al.[13].

C-glycosides can also be readily prepared by reaction of silyl enol ethers with various glycoside deriviatives in the presence of a Lewis acid catalyst. For example, reaction of silyl enol ethers with thiopyridyl glycosides in the presence of silver triflate to form C-glycosides is reported in R. M. Williams et al.[14] and A. O. Stewart et al.[15] Similarly, the formation of C-glycosides by reacting silyl enol ethers with sulfone glycosides under aluminum trichloride catalysis conditions is described in D. S. Brown et al.[16] Alternatively, silyl enol ethers can be reacted with 1-acetoxy glycosides in the presence of stannic chloride or trityl perchlorate to form C-glycosides. See, for example, K. Narasaka et al.,[17] S. Murata et al.,[18] T. Mukaiyama et al.[19] and M. Shimizu et al.[20] Silyl enol ethers can also be reacted with glycosyl imidates in the presence of a Lewis acid, such as zinc chloride, to form C-glycosides as reported in M. G. Hoffman et al.[21] Silyl enol ethers will also condense with glycosyl halides to afford C-glycosides. For example, silyl enol ethers have been reacted with glycosyl chlorides in the presence of a silver triflate catalyst as described in P. Allevi et al.[22] These reactions can also be used to prepared intermediates useful in this invention.

The 1-galactose derivatives of this invention where Y is —N(R$^1$)— (e.g., N-glycosides) can also be prepared by a variety of synthetic procedures well-known in the art. For example, protected amino ketones can be readily coupled with saccharides using art-recognized procedures and then N-acylated or sulfonylated and deprotected as illustrated in Scheme 3.

Scheme 3

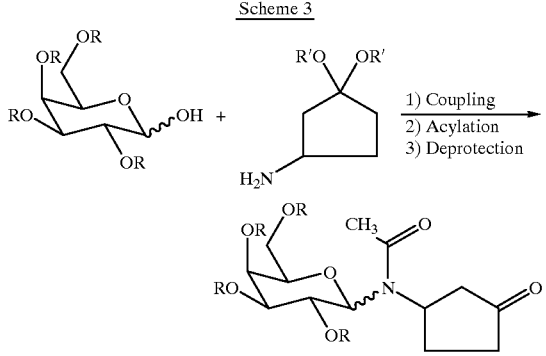

Preferred acylating agents for use in this reaction are those having the formula: R$^9$C(O)—L', wherein R$^9$ is preferably a hydrocarbyl group having from 1 (i.e., acetate) to about 20 carbon atoms (more preferably from 1 to 8 carbon atoms), and L' is a suitable leaving group. Typically, the leaving group, L', will be a halide, e.g., chloride or bromide; or a carboxylate group having the formula: —OC(O)R$^9$, wherein R$^9$ is as defined above. Alternatively, N-hydroxysuccinimide esters, and other activated esters well known in the art, can also be used. Representative examples of preferred acylating agents include, but are not limited to, acetyl chloride, acetic anhydride, propionyl chloride, propionyl anhydride, butanoyl chloride, and the like.

When an acyl halide is utilized in this reaction, at least one molar equivalent, based on the acyl halide, of a tertary amine, such as diisopropylethylamine, triethylamine, pyridine and the like, is preferably employed in the reaction to scavenge the acid generated during the reaction.

After forming a carbonyl-containing intermediate by, for example, any of the reactions described in Schemes 1–3 above or by any other art-recognized synthetic procedure, the carbonyl group of the intermediate is then reduced or reductively aminated to give an alcohol or an amine compound. These alcohol or amine compounds can then further reacted via reductive alkylation or by conversion to a leaving group and displacement to afford amines, ethers or thioethers and the like. The carbonyl-containing intermediate can also be reductively aminated to afford amines. Such reactions are well known to those of ordinary skill in the art and can be accomplished using art recognized procedures.

Figure 2:
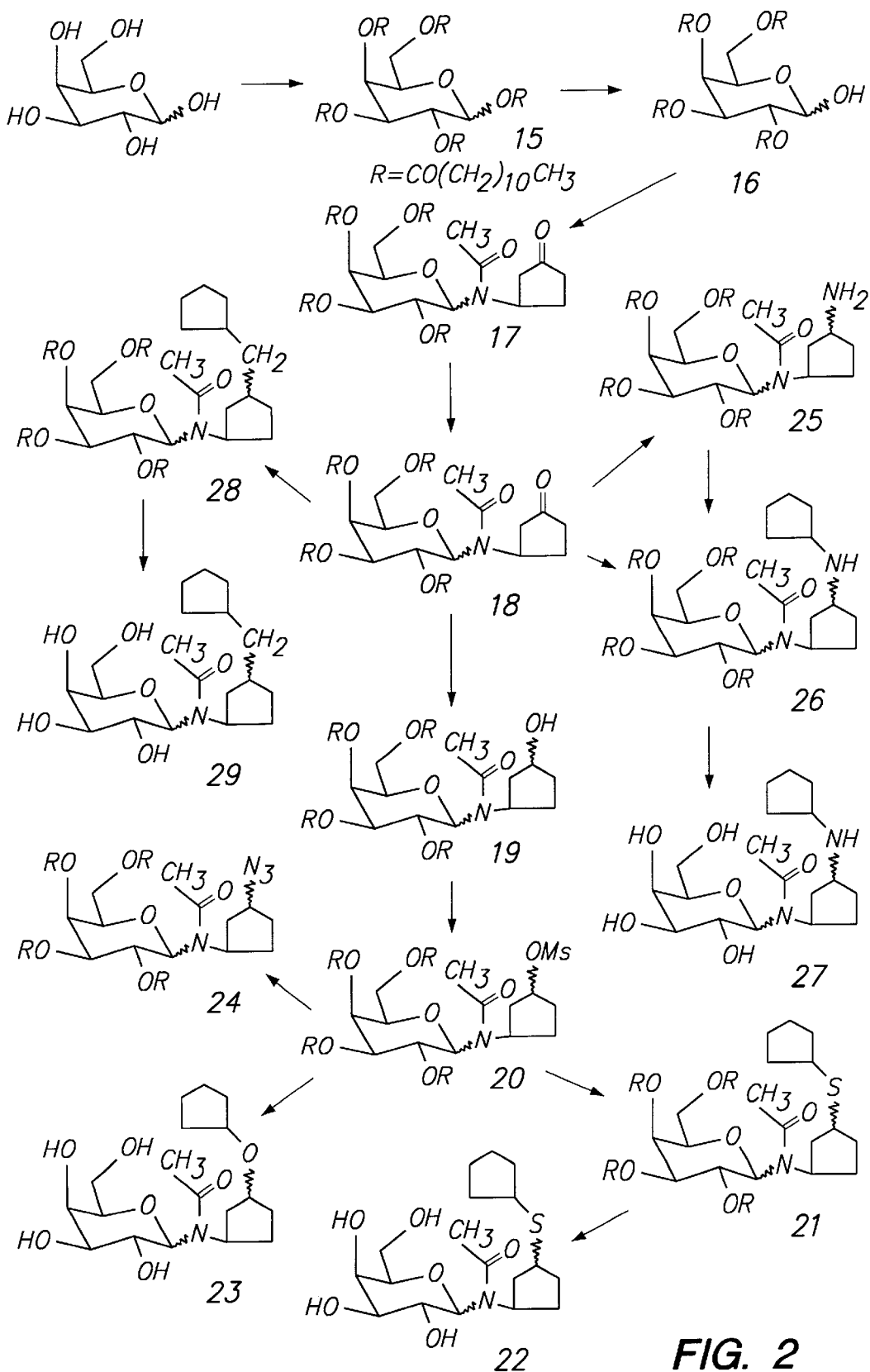
FIG. 2 illustrates a preferred reaction scheme which can be used to prepare various 1-galactose derivatives having a nitrogen-containing aglycon linking group.

The synthesis of various 1-galactose derivatives having either a carbon or a nitrogen-containing aglycon linkage is illustrated in FIGS. 1 and 2, respectively. It will be readily apparent to those of ordinary skill in the art that the synthetic procedure illustrated in FIGS. 1 and 2 and the following reaction conditions can be modified by selecting the appropriate starting materials and reagents to allow the preparation of other 1-galactose derivatives of this invention.

As shown in FIG. 1, C-(D-galactopyranosyl) nitromethane (prepared as described in O. R. Martin et al.,[8] L. Petrus et al.,[9] A. Fortsch et al.[10] and references cited therein) is perlauroylated by contacting D-galactose with at least 5 equivalents, and preferably 10 equivalents, of lauroyl chloride. This reaction is generally conducted in an inert diluent, such pentane, hexane, dichloromethane and the like, using a tertiary amine such as pyridine or triethylamine to neutralize the hydrochloric acid generated during the reaction. Preferably, a catalytic amount of 4-(N,N-dimethylamino)pyridine is added to the reaction mixture to facilitate this reaction. Typically, this reaction is conducted at a temperature of from about −78° C. to about 30° C. for about 0.5 to about 96 hours to afford C-(2,3,4,6-penta—O—lauroyl-α-D-galactopyranosyl) nitromethane, 1.

The Michael addition of compound 1 to cyclopent-2-en-1-one then affords C-(3-oxocyclopentan-1-yl)nitromethyl 2,3,4,6-tetra—O—lauroyl-1-thio-β-D-galactopyranoside, 2. This reaction is typically conducted by contacting 1 with at least one equivalent, preferably 1.0 to 1.2 equivalents, of cyclopent-2-en-1-one in the presence of an alkali metal fluoride salt, such as potassium fluoride, and a crown ether, such as 18-crown-6. Typically, this reaction is conducted in an inert diluent, such as acetonitrile, at a temperature of from about −40° C. to about 50° C. for about 1 to about 6 hours to afford compound 2.

The nitro group of compound 2 is then reduced to the corresponding hydride using tributyltin hydride and 2,2'-azobisisobutyronitrile (AIBN) to afford C-(3-oxocyclopentan-1-yl)methyl 2,3,4,6-tetra—O—lauroyl-β-D-galactopyranoside, 3. This reaction is typically conducted in refluxing toluene as described in O. R. Martin et al.[8] and reference cited therein.

The carbonyl group of compound 3 can then reduced using a reducing agent to provide for C-(3-hydroxycyclopent-1-yl)methyl 2,3,4,6-tetra—O—lauroyl-β-D-galactopyranoside, 4. Preferably, this reduction is conducted by contacting 3 with sodium borohydride, preferably about 1.2 to about 2.0 equivalents of sodium borohydride based on 3. Generally, this reaction is conducted in an inert diluent, such as tetrahydrofuran, isopropanol and mixture thereof, at a temperature of about 25° C. to about 30° C. for about 0.5 to about 3.0 hours. The resulting alcohol, 4, is readily purified by solid-phase extraction on C18 silica gel using pentane as an eluent.

The hydroxyl group of alcohol derivative 4 can then be converted into a leaving group, such as the mesylate, tosylate, etc., and displaced with various nucleophiles. For example, treatment of 4 with an excess, preferably about 1.1 to about 1.5 equivalents, of methanesulfonyl chloride in pyridine and an inert diluent, such as THF, affords C-(3-methanesulfonylcyclopent-1-yl)methyl 2,3,4,6-tetra—O—lauroyl-β-D-galactopyranoside, 5.

The mesylate group of 5 can then be displaced with, for example, a thiol compound of the formula HS-B (where B is as defined above) under basic conditions to provide a thioether. For example, treatment of 5 with about 1.0 to about 1.5 equivalents of cyclopentanethiol in the presence of a suitable base, such as DBU, in an inert diluent, such as toluene, affords C-[3-(thiocyclopentoxy)cyclopent-1-yl]methyl 2,3,4,6-tetra—O—lauroyl-β-D-galactopyranoside, 6.

The lauroyl groups can then be removed from compound 6 by contacting 6 with an excess of sodium methoxide in methanol and an inert diluent, such as dichloromethane, at about 25° C. to about 30° C. for about 1 to about 24 hours. Neutralization of the reaction mixture with Amberlite IR-SOS (H$^+$) resin then provides for C-[3-(thiocyclopentoxy)cyclopent-1-yl]methyl β-galactopyranoside, 7.

Alternatively, the mesylate group of compound 5 can be displaced with an alkali or alkaline earth metal alkoxide to afford ethers. Typically, this reaction is conducted by contacting an alcohol of the formula HO-B (where B is as defined above), such as cyclopentanol, with a strong base, such as sodium hydride, potassium hydride, calcium hydride and the like, in an inert diluent, such as tetrahydrofuran, toluene and the like, under substantially anhydrous conditions at a temperature in the range of from about −10° C. to about 120° C. for about 0.25 to about 3 hours.

The resulting alkali or alkaline earth metal alkoxide is generally not isolated, but is reacted in situ with the mesylate compound 5 to provide, after neutralization, an ether compound, e.g., C-[3-(cyclopentoxy)cyclopent-1-yl]methyl β-D-galactopyranoside, 8. This reaction is typically conducted in a substantially anhydrous diluent at a temperature of from about 0° C. to about 100° C. for about 2 to about 120 hours, followed by neutralization of the reaction mixture with Amberlite IR-SOS (H$^+$) resin. Suitable diluents for this reaction include, cyclopentanol, tetrahydrofuran, toluene and the like. Typically, the lauroyl groups of compound 5 are removed during the course of this reaction especially at higher temperature and when an excess of the alkali or alkaline earth metal alkoxide is employed.

The mesylate group of compound 5 can also be displaced with sodium azide to provide, e.g., C-(3-azidocyclopent-1-yl)methyl 2,3,4,6-tetra—O—lauroyl-β-D-galactopyranoside, 9. The azide displacement reaction is typically conducted by contacting the mesylate compound 5 with an excess, preferably about 5 to about 50 equivalents of sodium azide in an inert diluent, such as N,N-dimethylformamide, THF, and mixtures thereof, at a temperature of from about 50° C. to about 100° C. for about 1 to about 6 hours. Preferably, a crown ether, such as 18-crown-6, is added to the reaction mixture to promote the displacement reaction.

The azido intermediate 9 can then be reduced with a reducing agent to afford the corresponding primary amine, i.e., compound 10. Preferably, this reaction is conducted by contacting the azido compound with about 1.0 to about 1.1 equivalents of sodium borohydride and about 2.0 to about 2.2 equivalents of nickel chloride (NiCl$_2$) in an inert diluent, such as ethanol, isopropanol, or mixtures thereof, at a temperature of from about 0° C. to about 50° C. for about 0.5 to about 6 hours.

Alternatively, compound 3 can be reductively aminated to provide for compound 10 directly. In one embodiment of this reaction, compound 3 is contacted with an excess of ammnonium acetate and at least one equivalent of sodium cyanoborohydride based on 3. This reaction is typically conducted in an inert diluent, such as methanol, tetrahydrofuran and mixtures thereof, at a temperature of about 25° C. to about 30° C. for about 1 to about 72 hours.

In another preferred embodiment, the reductive amination reaction is accomplished by contacting compound 3 with an excess of ammonium acetate and an excess of trimethyl orthoformate based on 3, in an inert diluent, such as 1,2-dichloroethane at a temperature of about 25° C. to about 30° C. for about 12 to about 72 hours to form an imine intermediate. The imine intermediate is generally not isolated but is contacted in situ with an excess of sodium borohydride, preferably about 1.2 to about 1.5 equivalents of sodium borohydride, based on 3. The resulting amino compound 10 is then readily purified by solid-phase extraction on C18 silica gel using pentane as an eluent.

The primary amine group of compound 10 can then be reductively alkylated using a cyclic ketone, such as cyclopentan-1-one, to afford a secondary amine, e.g., C-[3-(cyclopentylamino)cyclopent-1-yl]methyl 2,3,4,6-tetra—O—lauroyl-β-D-galactopyranoside, 11. Typically, this reaction is conducted by contacting the primary amine with an excess, preferably about 2 to about 500 equivalents of an aldehyde or a ketone in the presence of at least one equivalent, preferably about 1.0 to about 10 equivalents, of a reducing agent, such as sodium triacetoxyborohydride. This reaction is typically conducted in an inert diluent, such as dichloromethane, methanol, or mixtures thereof, at a temperature of about 0C to about 50° C. for about 10 to about 48 hours.

As shown in FIG. 1, compound 3 can also be reductively aminated with an amine compound of the formula H$_2$N—B (where B is as defined above), such as cyclopentylamine, to provide a secondary amine compound, e.g., compound 11. Specifically, compound 3 is contacted with a molar excess of the amine compound, preferably with 10 equivalents based on 3, in the presence of at least one molar equivalent, preferably about 1.0 to about 1.2 equivalents, of sodium cyanoborohydride. Typically, this reaction is conducted in an essentially anhydrous inert diluent, such as acetonitrile, at a temperature of about 25° C. to about 30° C. for about 1 to about 72 hours. The resulting secondary amine 11 is readily purified by solid-phase extraction on C18 silica gel using pentane as the eluent.

The lauroyl groups of compound 11 are then removed by contacting the lauroyl-protected compound with an excess of sodium methoxide in methanol and an inert diluent, such as dichloromethane, at about 25° C. to about 30° C. for about 1 to about 24 hours. Neutralization of the reaction mixture with Amberlite IR-50S (H$^+$) resin then provides C-[3-(cyclopentylamino)cyclopent-1-yl]methyl β-D-galactopyranoside, 12.

Additionally, compound 3 can be reacted with an ylide of a phosphonium salt (i.e., a Wittig reagent), such (cyclopentylmethyl) (triphenyl)phosphonium bromide, to afford, after hydrogenation of the resulting olefin, C-[3-(cyclopentylmethyl)cyclopent-1-yl]methyl 2,3,4,6-tetra—O—lauroyl-β-D-galactopyranoside, 13. This reaction is typically conducted by first contacting the phosphonium salt with a slight excess, preferably about 1.1 to about 1.2 equivalents, of a strong base, such as n-butyl lithium, in an inert diluent, such as diethyl ether, THF and the like, at a temperature of from about −78° C. to about 0° C. for 0.5 to 6 hours to form the ylide. Typically, the ylide is not isolated but is reacted in situ with a carbonyl compound, such as 3, to afford an olefin. The resulting olefin can then readily hydrogenated by treatment with hydrogen in the presence of a catalyst, such as Pd/C, in an inert diluent, such as ethanol, at a temperature of from about 0° C. to about 50° C. for about 1 to 48 hours to provide compound 13. Removal of the lauroyl from compound 13 using excess sodium methoxide in methanol, followed by neutralization of the reaction mixture with Amberlite IR-50S (H$^+$) resin then affords C-[3-(cyclopentylmethyl)cyclopent-1-yl]methyl β-galactopyranoside, 14.

As noted above, FIG. 2 illustrates the synthesis of various 1-galactose derivatives having a nitrogen-containing aglycon linking group. As shown in FIG. 2, D-galactose is perlauroylated by contacting D-galactose with at least 5 equivalents, and preferably 10 equivalents, of lauroyl chloride. This reaction is generally conducted in an inert diluent, such pentane, hexane, dichloromethane and the like, using a tertiary amine such as pyridine or triethylamine to neutralize the hydrochloric acid generated during the reaction. Preferably, a catalytic amount of 4-(N,N-dimethylamino) pyridine is added to the reaction mixture to facilitate this reaction. Typically, this reaction is conducted at a temperature of from about −78° C. to about 30° C. for about 0.5 to about 96 hours to afford 1,2,3,4,6-penta—O—lauroyl-α-D-galactopyranose, 15, in approximately 70% yield from D-galactose.

The 1-lauroyl group of compound 15 is then selectively removed to provide 2,3,4,6-tetra—O—lauroyl-β-D-galactopyranose, 16, by contacting 15 with at least one equivalent, preferably 1 to 1.2 equivalents, of benzylamine. This reaction is typically conducted at about 60° C. to about 100° C. for about 1 to about 96 hours to provide for compound 16.

Compound 16 is then coupled with 3-aminocyclopentan-1-one dimethyl ketal to give, after acetylation and deprotection, 1-(2-oxocyclopentan-1-yl)acetamido-2,3,4,6-tetra—O—lauroyl-β-D-galactopyranoside, 17. This reaction is typically conducted by contacting 16 with at least one equivalent, preferably 1 to about 2 equivalents, of 3-aminocyclopentan-1-one dimethyl ketal in an inert diluent, such as methanol and the like, at a temperature ranging from about 20° C. to about 100° C. The reaction is generally complete in about 12 to about 72 hours. Preferably, a catalytic amount of acetic acid or a similar acid is employed in this reaction. Additionally, a dehydrating agent, such as molecular sieves, may be employed in this reaction.

The protected amino ketones employed in this reaction may be prepared from known starting materials and reagents using conventional procedures. For example, 3-hydroxycyclopentan-1-one can be readily protected as the dimethyl ketal or as the ethylene ketal using methanol or ethylene glycol, respectively, and an acid catalyst, such as p-toluenesulfonic acid. The hydroxyl group can then be readily converted into a leaving group, such as the mesylate, tosylate and the like, by treatment, for example, with excess methanesulfonyl chloride in pyridine and an inert diluent, such as THF. The mesylate group can then be displaced with sodium azide to provide, after reduction of the azido group, a primary amine compound. The azide displacement reaction is typically conducted by contacting the mesylate compound with an excess of sodium azide in an inert diluent, such as DMF, THF and mixture thereof and the like. Preferably, a crown ether, such as 18-crown-6, is added to the reaction mixture to promote the displacement reaction. The azido group can then be reduced with a reducing agent, such as sodium borohydride in the presence of nickel chloride, to afford 3-aminocyclopentan-1-one dimethyl ketal. Other conventional protecting groups may also be employed to protect the carbonyl group of the amino ketone to prevent undesired dimerization or polymerization including, by way of illustration, various ketals, thioketals and the like.

After the coupling reaction, the resulting intermediate, 1-(2-oxocyclopentan-1-yl)amino-2,3,4,6-tetra—O—lauroyl-β-D-galactopyranoside, is then N-acylated with excess acetic anhydride using conventional reaction conditions. Preferably, this acylation reaction is conducted at a temperature in the range of about −70° C. to about 70° C. in a diluent that is essentially inert under the reaction conditions, such as methanol, ethanol, chloroform, toluene and the like, for about 0.5 to about 24 hours. The dimethyl ketal protecting group is then removed using conventional reagents and conditions, such as aqueous acid and the like, to afford 17.

Compound 17 can then be reacted using essentially the same reagents and conditions described above for compound 3 to afford various 1-galactose derivatives, e.g., compounds 18–29, as illustrated in FIG. 2.

Optionally, the 1-galactose derivatives of formula I wherein Y' is a sulfide linking group (—S—) can be oxidized using conventional reagents and conditions to provide the corresponding sulfoxide (Y'=—S(O)—) and sulfone (Y'=—SO$_2$—) derivatives. Suitable reagents for oxidizing a sulfide compound to a sulfoxide include, by way of example, hydrogen peroxide, peracids such as 3-chloroperoxybenzoic acid (MCPBA), sodium periodate, sodium chlorite, sodium hypochlorite, calcium hypochlorite, tert-butyl hypochlorite and the like. Chiral oxidizing reagents (optically active reagents) may also be employed to provide chiral sulfoxides. Such optically active reagents are well known in the art and include, for example, the reagents described in Kagen et al.[23] and references cited therein.

The oxidation reaction is typically conducted by contacting the 1-galactose derivative with about 0.95 to about 1.1 equivalents of the oxidizing reagent in an inert diluent, such as dichloromethane, at a temperature ranging from about 0° C. to about 50° C. for about 1 to about 48 hours. The resulting sulfoxide can then be further oxidized to the corresponding sulfone by contacting the sulfoxide with at least one additional equivalent of an oxidizing reagent, such as hydrogen peroxide, MCPBA, potassium permanganate and the like. Alternatively, the sulfone can be prepared directly by contacting the sulfide with at least two equivalents, and preferably an excess, of the oxidizing reagent.

If desired, the hydroxyl groups of the galactose moiety may be readily acylated, sulfonylated or phosphorylated using art recognized procedures and reagents to provide compounds of formula I wherein at least one of $R^a$, $R^b$, $R^c$, and $R^d$ is —O—SO$_2$—OH, —C(O)R$^7$ or —P(O)(OR$^8$)$_2$ or pharmaceutically acceptable salts thereof, where $R^7$ and $R^8$ are as defined above. Such acylation reactions may occur as an initial step of the synthesis (i.e., using an acyl halide, such as lauroyl chloride, as described above) or as a post-synthetic transformation of compounds of formula I where $R^a$, $R^b$, $R^c$, and $R^d$ are each hydrogen using, for example, acyl halides, anhydrides, halophosphates, sulfur trioxide, and the like.

For example, a de-blocked hydroxyl group can be sulfonylated by treating the hydroxy-containing compound with an excess, preferably about 1.1 to about 1.2 equivalents, of a pyridine:sulfur trioxide complex in an inert diluent, such as N,N-dimethylformamide, at ambient temperature for about 1 to about 24 hours. Typically, the resulting sulfate (i.e., —O—SO$_2$—OH) is isolated as its salt by treatment with, for example, a Na$^+$ resin in an inert diluent, such as methanol. Further reaction conditions suitable for forming sulfates and phosphates can be found, for example, in U.S. Pat. No. 5,580,858[24].

In another embodiment of this invention, the 1-galactose derivatives of this invention can be attached to a support, preferably a solid support, either through the galactose moiety or through the A or B portions of the molecule. Methods for attaching compounds to supports through various functional groups are well known in the art and any of these known methods may be employed to covalently attach the 1-galactose derivatives of this invention to a support.

By way of example, a 1-galactose derivative of formula I wherein A or B contains a carboxylic acid moiety can be covalently attached to an aminated solid support using conventional coupling procedures and reagents. Typically, such a coupling reaction will be conducted using well-known coupling reagents such as carbodiimides, BOP reagent (benzotriazol-1-yloxy-tris(dimethylamino) phosphonium hexafluorophosphonate) and the like. Suitable carbodiimides include, by way of example, dicyclohexyl-carbodiimide (DCC), diisopropylcarbodiimide, 1-(3-dimethylaminopropyl)-3-ethylcarbodiimide (EDC) and the like. Preferably, a well-known coupling promoter, such as N-hydroxysuccinimide, 1-hydroxybenzotriazole and the like, is also employed in the reaction mixture to facilitate the coupling reaction.

The coupling reaction is typically conducted by contacting the solid support with an excess, preferably about 1.1 to about 10 or more equivalents, of the 1-galactose derivative (based on the number of equivalents of amino groups present on the solid support) and at least one equivalent, preferably about 1.5 to about 3.0 equivalents, of the coupling reagent (based on the 1-galactose derivative) in an inert diluent, such N,N-dimethylformamide and the like. If desired, least one equivalent, preferably about 1.5 to about 3.0 equivalents (based on the 1-galactose derivative), of a coupling promoter such as 1-hydroxybenzotriazole may also be used in the reaction. Generally, the coupling reaction is conducted at a temperature ranging from about 0° C. to about 50° C. for about 24 to about 100 hours. Upon completion of the reaction, the solid support is preferably contacted with excess acetic anhydride in methanol at a temperature ranging from about 0° C. to about 40° C. for about 12 to about 24 hours to cap any unreacted amino groups present on the solid support. The yield of incorporation of the 1-thiogalactose derivative onto the solid support can be determined using well-established procedures such as those described, for example, by M. Dubois et al.[25].

The 1-galactose derivatives of this invention can also be prepared on a solid support via solid-phase synthesis techniques. Typically, such solid-phase techniques involve first covalently attaching a 1-galactose compound through a hydroxyl group on the galactose moiety to a solid support using conventional procedures and reagents. The covalently-bound 1-galactose compound is then reacted using the procedures described above to form a carbonyl-containing intermediate. The resulting carbonyl-containing intermediate is then reduced or reductively aminated to give an alcohol or an amine compound which can be further derivatized as described herein.

By way of example, 1-β-D-galactopyranoside intermediates can be readily attached to a trityl chloride resin having about 0.80 to about 1.00 mmol/g of active chlorine by contacting the resin with about 0.75 to about 2.0 equivalents of 1-β-D-galactopyranoside intermediate in pyridine containing a catalytic amount of 4-(N,N-dimethylamino) pyridine at a temperature ranging from about 25° C. to about 100° C. for about 12 to 48 hours. The resulting covalently bound 1-β-D-galactopyranoside intermediate is then reacted as described above to afford a 1-thiogalactose derivative of formula I covalently attached to the solid support resin. If desired, the 1-thiogalactose derivative can be cleaved from the solid support resin by contacting the resin with an excess of trifluoroacetic acid and triisopropylsilane in an inert diluent, such as dichloromethane, at ambient temperature.

Utility

In one embodiment, the compounds of this invention are useful in blocking binding of a toxin, such as heat-labile enterotoxin or cholera toxin, to its receptor either in vitro or in vivo. In another embodiment, the compounds of this invention inhibit binding of an organisms (e.g., bacteria, virus, fungi, and the like), such as *Vibrio cholerae* and enterotoxigenic strains of *Escherichia coli*, to its cell surface receptor.

Accordingly, the compounds of this invention can be used to ameliorate conditions associated with infection by an organism, including gastrointestinal infections caused by enterovirulent organisms, such as *Vibrio cholerae* or enterotoxigenic strains of *Escherichia coli*, including, by way of example, diarrhea, intestinal bleeding, abdominal pain, and the like.

When used in treating or ameliorating such conditions, the compounds of this invention are typically delivered to a patient in need of such treatment by a pharmaceutical composition comprising a pharmaceutically acceptable diluent and an effective amount of at least one compound of this invention. The amount of compound administered to the patient will vary depending upon what compound and/or composition is being administered, the purpose of the administration, such as prophylaxis or therapy, the state of the patient, the manner of administration, and the like. In therapeutic applications, compositions are administered to a patient already suffering from an infection, such as gastrointestinal infections associated with, for example, *Vibrio cholerae* or enterotoxigenic strains of *Escherichia coli*, in an amount sufficient to at least partially arrest further onset of the symptoms of the disease and its complications. An amount adequate to accomplish this is defined as "therapeutically effective dose." Amounts effective for this use will depend on the judgment of the attending clinician depending upon factors such as the degree or severity of the infection in the patient, the age, weight and general condition of the patient, and the like. Preferably, for use as therapeutics, the compounds described herein are administered at dosages ranging from about 0.1 to about 10 mg/kg/day.

Such pharmaceutical compositions may contain more than one compound of the present invention. For example, they may contain one compound of formula I which is highly effective at inhibiting the binding of LT and a different compound of formula I which is highly effective at inhibiting the binding of enterotoxigenic E. coli to cell surface receptors.

When a support having a compound of formula I' covalently attached is used for treating or ameliorating conditions associated with gastrointestinal infections, supports which are non-toxic, resistant to mechanical and chemical decomposition are preferred. Those supports which pass unaffected through the gut and which are completely and rapidly eliminated following oral administration are most preferred, since such supports provide for rapid clearance of the toxin and/or pathogen from the subject.

As noted above, the compounds administered to a patient are in the form of pharmaceutical compositions described above which can be administered by a variety of routes including oral, rectal, transdermal, subcutaneous, intravenous, intramuscular, etc. These compounds are effective as both injectable and oral deliverable pharmaceutical compositions. Such compositions are prepared in a manner well known in the pharmaceutical art and comprise at least one active compound.

The pharmaceutical compositions are formulated in the presence of a pharmaceutically acceptable carrier. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, etc., containing, for example, up to 10% by weight of the active compound, soft and hard gelatin capsules, suppositories, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The 1-galactose derivatives of this invention can also be administered in the form of pro-drugs, i.e., as derivatives which are converted into a biologically active compound of formula I in vivo. Such pro-drugs will typically include compounds of formula I in which at least one of $R^a$, $R^b$, $R^c$, or $R^d$ is a biologically liable group, such as —C(O)$R^7$ or —P(O)(O$R^8$)$_2$, where $R^7$ and $R^8$ are as defined above.

The following synthetic and biological examples are offered to illustrate this invention and are not to be construed in any way as limiting the scope of this invention. Unless otherwise stated, all temperatures are in degrees Celsius.

EXAMPLES

In the examples below, the following abbreviations have the following meanings. If an abbreviation is not defined, it has its generally accepted meaning.

| | |
|---|---|
| Å = | angstroms |
| bd = | broad doublet |
| bs = | broad singlet |
| BSA = | bovine serum albumin |
| d = | doublet |
| dd = | doublet of doublets |
| DMAP = | dimethylaminopyridine |
| eq. = | equivalents |
| g = | grams |
| L = | liter |
| m = | multiplet |
| meq = | milliequivalent |
| mg = | milligram |
| mL = | milliliter |
| mmol = | millimole |
| N = | normal |
| OPD = | o-phenylenediamine |
| PBS = | phosphate buffered saline at pH 7.2 |
| q = | quartet |
| quint. = | quintet |
| s = | singlet |
| t = | triplet |
| TFA = | trifluoroacetic acid |
| THF = | tetrahydrofuran |
| TLC = | thin layer chromatography |
| Tween 20 = | polyoxyethylenesorbitan monolaurate |
| μL = | microliter |

$^1$H-Nmr spectra were recorded with a Brueker AM-360 spectrometer and MALDI-TOF mass spectra were recorded with a HP G2020A (LD-TOF) instrument. Optical rotations were measured with a Perkin-Elmer 241 polarimeter. Reactions were monitored by TLC on Silica Gel FG254 (E. Merck, Darmstadt, Germany).

Example A

Solid-Phase Extraction of Lauroylated Intermediates

As indicated in the following examples, certain lauroylated reaction intermediates were purified by solid-phase extraction. In this purification procedure, the reaction mixture is concentrated, re-dissolved in methanol, and applied onto C18 silica (Waters Prep C18, 125 Å, 1 g per 20 mg lauroylated carbohydrate). The C18 silica is then washed with methanol (10 mL/ g C18 silica) and the product is eluted with pentane (10 mL/ g C18 silica). For L-arginine containing compounds, the reaction mixture is concentrated, re-dissolved in 70% methanol and applied onto C18 silica. The C18 silica is then washed with 70% methanol and the product is eluted with methanol. The resulting product contains no residual reagents as determined by TLC, $^1$H-nmr, or MALDI-TOF mass spectroscopy.

Example 1

Synthesis of C-(2,3,4,6-Tetra—O—lauroyl-β-D-galactopyranosyl) Nitromethane (2)

The title compound can be prepared from D-galactose using the procedures described in O. R. Martin et al.,[8] L. Petrus et al.,[9] A. Fortsch et al.[10] and references cited therein.

Example 2

General Procedure for Michael Additions

Using the procedures described O. R. Martin et al.[8] and references cited therein, compound 2 and a cyclic α,β-unsaturated ketone can be reacted in dry acetonitrile (8 mL) under argon in the presence of potassium fluoride and 18-crown-6 to afford the Michael adduct. The nitro group can then be reduced as described in the Martin reference.

The residue can be purified by column chromatography on $SiO_2$ by eluting with pentane/EtOAc. The products can be characterized with $^1$H-nmr spectroscopy and MALDI-TOF mass spectroscopy.

Example 3

Synthesis of 1,2,3,4,6-Penta—O—lauroyl-α-D-galactopyranose 15

To a suspension of galactose (3.78 g, 21.0 mmol), pyridine (50 mL), and 4-dimethylaminopyridine (cat.) in pentane (150 mL) under argon atmosphere, was added lauroyl chloride (50 mL, 210 mmol) at −78° C. The mixture was allowed to reach ambient temperature. The resulting white slurry slowly dissolved and a fine precipitate of pyridinium hydrochloride formed. After 40 h, the pyridinium hydrochloride was filtered off and the pentane solution was concentrated. Column chromatography ($SiO_2$, pentane/EtOAc 9:1) gave 15 (16.0 g, 70% yield), $[\alpha]_D^{25}$+39° (c 0.9, $CHCl_3$). $^1$H-Nmr data ($CHCl_3$): δ6.39 (d, 1H, J 2.4 Hz, H-1), 5.51 (br s, 1H, H-4), 5.35 (m, 2H, H-2 and H-3), 4.32 (br t, 1H, J 6.6 Hz, H-5), 4.08 (d, 2H, J 6.6 Hz, H-6a and H-6b), 2.39, 2.38, 2.30, 2.26 (4 t, 2H each, J 7.5 Hz, —$CH_2$CO—), 2.21 (m, 2H, —$CH_2$CO—), 0.88 (t, 15 H, J 7.0 Hz, —CH3). Anal. Calcd for $C_{66}H_{122}O_{11}$: C, 72.2; H, 11.3. Found: C, 72.6; H, 11.5.

Example 4

Synthesis of 2,3,46-Tetra—O—lauroyl-β-D-galactopyranose (16)

To compound 15 (from Example B, 276.5 mg, 0.253 mmol) in dry tetrahydrofuran (2.0 mL) under argon, was added benzylamine (27.9 μL, 0.255 mmol). The mixture was concentrated after 70 h to afford the title compound.

Example 5

Synthesis of 1-(2-oxocyclopentan-1-yl)acetamido-2,3,4,6-tetra—O—lauroyl-β-D-galactopyranoside (17)

2,3,4,6-Tetra—O—lauroyl-β-D-galactopyranose (16) (1 eq.) and 3-aminocyclopentan-1-one dimethyl ketal (1.5 eq.) are stirred in methanol, containing a catalytic amount of acetic acid, at a temperature of about 20° C. to about 30° C. for about 48 hours. The reaction mixture is then concentrated in vacuo. The residue is dissolved in toluene and an excess of acetic anhydride is added. This reaction mixture is then stirred at about 25° C. for about 24 hours. Concentration of the reaction mixture in vacuo affords a residue which is stirred with lithium tetrafluoroborate in wet acetonitrile to provide the title compound.

Example 6

General Procedure for Reduction to Alcohols

To the product from Example 2 or 5 (100 μmol) in dry tetrahydrofuran (2.0 mL) and isopropanol (0.7 mL) under argon atmosphere, is added $NaBH_4$ (150 μmol). After 0.5–3 h, the mixture is concentrated and the residue is purified according to the solid-phase extraction procedure of Example A. The product alcohols are characterized with $^1$H-nmr spectroscopy and MALDI-TOF mass spectroscopy.

Example 7

General Procedure for Reductive Amination to a Primary Amine

Method 1: To the product from Example 2 or 5 (100 μmol) and ammonium acetate (75 mg, 1 mmol) in dry methanol (2.3 mL) and tetrahydrofuran (0.9 mL) under argon, is added $NaCNBH_3$ (100 μmol). After 1–72 h, the mixture is concentrated and the residue purified according to the solid-phase extraction procedure of Example A. The product amines are characterized with $^1$H-nmr spectroscopy and MALDI-TOF mass spectroscopy.

Method 2: The product from Example 2 or 5 (200 mg, 0.198 mmol) and dry $NH_4OAc$ (30 mg, 0.4 mmol) is stirred in dry MeOH (6 mL), dry 1,2-dichloroethane (6 mL), and trimethyl orthoformate (1 mL) under argon for 24 h (until TLC analysis showed that most of the starting material is consumed). $NaBH_4$ (10 mg, 0.26 mmol) is added and after 1 h the mixture is concentrated. The residue is purified according to the solid-phase extraction procedure of Example A to provide the primary amine (containing traces of the corresponding alcohol). This mixture is dissolved in pentane/EtOAc (1:1) and applied onto a Waters Sep-Pak Plus Longbody $SiO_2$ cartridge. The cartridge is washed with pentane/EtOAc (1:1, 20 mL) (to remove the corresponding alcohol), followed by elution with toluene/EtOH (9:1, 30 mL) to afford the primary amine.

Example 8

General Procedure for the Preparation of Mesylates

To the alcohol from Example 6 (0.3 mmol) in dry tetrahydrofuran (2 mL) and dry pyridine (4 mL) under an argon atmosphere is added methanesulfonyl chloride (0.5 mL). After 12–24 h, the mixture is washed with 0.5M HCl and extracted with pentane. The pentane extracts are concentrated and the residue is purified on C18-silica gel chromatography to afford the mesylate derivative.

Example 9

General Procedure for the Preparation of Azido Compounds

To the mesylate from Example 8 (0.2 mmol) in dry DMF (8 mL) and dry THF (3 mL) under an argon atmosphere at 60° C. is added sodium azide (5 mmol) and 18-crown-6 (180 mg). After 2 hours, the reaction mixture is concentrated and the residue is purified on C18-silica. In some cases, the product is re-chromatographed with silica gel using pentane/EtOAc (9:1) as the eluant to afford the azido derivative.

Example 10

General Procedure for Reduction of Azido Groups to Primary Amines

To a solution of the azido compound from Example 9 (15 μmol) in dry isopropanol (1 mL) and dry ethanol (1 mL) under an argon atmosphere, is added $NaBH_4$ (15 μmol) and $NiCl_2$ (30 μmol). After 1 hour, the reaction mixture is neutralized with acetic acid (1 drop), concentrated and purified on C18-silica to afford the primary amine.

Example 11

General Procedure for Reductive Alkylation of Primary Amines

To the primary amine from Example 7 or 10 (6.8 μmol) in dry methanol (1 mL) and dry dichloromethane (1 mL) under an argon atmosphere is added an aldehyde or ketone (3.4 mmol) and sodium triacetoxyborohydride (47 μmol). After 24–48 hours, toluene (1 mL) is added and the mixture is concentrated and the residue purified on C18-silica gel.

Example 12

General Procedure for Reductive Amination

To the product from Example 2 or 5 (0.1 mmol) and an amine (0.45 mmol) in dry dichloromethane (2 mL), methanol (2 mL) and triethylorthoformate (1 mL) under argon, is added $NaCNBH_3$ (1 mmol). After 24 h, the mixture is concentrated and dissolved in toluene (1 mL) and purified on C18-silica gel (5 g).

Example 13

General Procedure for Deblocking 2,3,4,5-tetra—O—lauroyl 1-Galactose Derivatives To the O-lauroylated 1-galactose derivative (100 µmol) in dry methanol (7.1 mL) and dichloromethane (1.4 mL) under argon, is added methanolic sodium methoxide (1M, 50 µL). After 1–24 h, the mixture is neutralized with Amberlite IR-50S ($H^+$) resin, filtered and concentrated. The residue is dissolved in dichloromethane/methanol 2:1 and applied to a Waters SepPak Plus Longbody $SiO_2$ cartridge. The cartridge is washed with dichloromethanel methanol (2:1) and then the product is eluted with dichloromethane/ methanol/water (5:5:1) (20 mL) and concentrated. The residue is dissolved in water and applied onto a column of C18 silica (Waters Prep C18, 125 Å, 5 g). The C18 silica is washed with water (50 mL) and then the product is eluted with methanol (50 mL). The resulting secondary amines are characterized with 1H-nmr spectroscopy and MALDI-TOF mass spectroscopy.

Example 14

Attachment of a Carboxyl-Containing 1-β-D-galactopyranoside to a Solid Support To a 1-β-D-galactopyranoside of formula I having a carboxyl group on the A or B ring (2.1 mg, 4.5 µmol), silyl aminated Chromosorb P (449 mg, prepared as described in U.S. Pat. No. 4,137,401[26] and Westal et al.[27]), and hydroxybenzotriazole (1.3 mg, 9.4 µmol) in DMF (1 mL, dried over 4 Å molecular sieves), is added diisopropylcarbodiimide (1.4 µL, 9.0 µmol). The beads are filtered off after 75 hours, washed with water, DMF, MeOH, and $CH_2Cl_2$. To the resulting beads in MeOH (1.5 mL) is added acetic anhydride (0.5 mL) and after 16.5 hours, the beads are filtered and washed with water, DMF, MeOH, $CH_2Cl_2$, and pentane. Fine particles are removed by suspending the beads in MeOH and decanting the supernatant repeatedly. Drying under high-vacuum provides a product having the 1-β-D-galactopyranoside covalently attached to the chromasorb P by formation of an amide linkage between amine group of the chromasorb P and the carboxy group of the 1-galactose derivative. Phenol/$H_2SO_4$ assay using the procedure described in M. Dubois et al.[25] can be used to show the incorporation yield.

Example 15

Inhibition of Heat-Labile Enterotoxin Binding to $G_{D1b}$

Using this example, the 1-galactose derivatives of formula I above could be tested for their ability to inhibit the binding of heat-labile enterotoxin from *E. coli* to ganglioside $G_{D1b}$. The bioassay is conducted using the procedure described by A.-M. Svennerholm[28] except that ganglioside $G_{D1b}$ is used instead of ganglioside $G_{M1}$. The compounds of this invention are expected to inhibit binding of heat-labile enterotoxin to ganglioside $G_{D1b}$ by at least 20% in this assay.

Example 16

Inhibition of Cholera Toxin Binding to $G_{D1b}$

In this example, 1-galactose derivatives of formula I above could be tested for their ability to inhibit the binding of cholera toxin to ganglioside $G_{D1b}$. This bioassay can be conducted using the following modification of the procedure described by A.-M. Svennerholm[28].

On day 1, microtiter plates (C96 Maxisorp) are coated with 100 µL of 1 mg/mL GD1b (disialoganglioside GD1b, MW=2127, Fluka) in PBS per well and incubated overnight at 37° C.

On day 2, the samples to be tested are diluted in BSA-Tween-PBS (0.1% BSA and 0.05% Tween-20 in PBS; Sigma). A total of 500 µL of each solution is prepared so that each point could be measured in quadruplicate. A concentration curve of 10, 20 and 30 ng/mL of CTB5-HRP (CT-B5 conjugated to HRP, Sigma, lyophilized, diluted in Tween-PBS) is prepared. For the inhibition experiments, 20 ng/mL of CTB5-HRP is used. The samples are then incubated for 2 hours at room temperature. After incubation, the plates were emptied and unattached ganglioside was removed by washing the plates 2 times with 200 µL PBS per well. Additional binding sites on the plastic surface are then blocked by incubating the plates with 200 µL of 1 % BSA in PBS per well for 30 minutes at 37° C. The plates are then emptied and unattached BSA is removed by washing the plates 3 times with 200 µL of 0.05 % Tween 20-PBS per well. Samples (100 µL) are added to 4 different wells and incubated for 30 minutes at room temperature. The plates are emptied and unattached BSA is removed by washing the plates 3 times with 200 µL of 0.05 % Tween 20-PBS per well.

A substrate solution is freshly prepared for each ELISA. Each solution contained 10 mg of σ-phenylenediamine (Sigma), 5 mL of 0.1M sodium citrate (filter sterile or autoclaved), 5 mL of 0.1M citric acid (filter sterile or autoclaved) and 4 mL of 30% $H_2O_2$. (Gloves should be worn since σ-phenylenediamine is carcinogenic). The substrate solution (100 µL) is then added to each well and incubated for 30 minutes at room temperature. After incubation, the $OD_{450}$ is recorded.

Under the conditions of the assay, D-galactose had an $IC_{50}$ of 30 mM. The compounds of this invention are expected to inhibit binding of cholera toxin to ganglioside $G_{D1b}$ by at least 10% in this assay.

Example 17

Neutralization of the Cytotonic Activity of CT and LT

This example illustrates how the solid support material of Example 2 could be tested for its ability to neutralize the cytotonic activity of CT and LT. The cytotonic activity of CT and LT is measured by the use of Chinese hamster ovary cells (CHO) that are maintained in Hams F12 media supplemented with 10% fetal bovine serum (FBS) in an atmosphere of 5% $CO_2$ at 37° C. Toxin samples are diluted 1:5 in Hams media and filter sterilized through 0.22 micron syringe filters. Samples are then serial 5-fold diluted in media and 100 µL of each dilution is added to wells with confluent monolayers of CHO cells and incubated for 24 h at 37° C. (under 5% $CO_2$). Each sample is analyzed two times. Cytotonic effects are readily visible after 24 h incubation by comparing wells with controls that do not contain toxin. After 24 h, the cells are fixed with 95% methanol and stained with Geimsa stain. Toxin containing samples from neutralization experiments are treated in an analogous fashion except that the percent neutralization is determined by comparing the endpoint dilutions of samples with and without the solid support material of Example 2.

A solution containing purified CT or LT (2, 10 or 20 pug in 1 mL PBS) is added to the solid support material of Example 2 (20 mg) in 1.5 mL microcentrifuge tubes and incubated at room temperature for 1 h on an end-over rotator. After incubation, the solid support material is allowed to settle to the bottom of the tubes and the supernatants are carefully removed. The supernatants are added to CHO cells and the cytotonic endpoint determined after incubation for 24 h as described above. The extent of reduction in the endpoint in the presence of the solid support material is determined by comparing with controls in which solid support material is not added.

A solid support material of Example 2 is expected to neutralized more than 90% of CT and LT activity, i.e., less than 10% toxin activity will remain.

Example 18

Inhibition of Colonization Factor Antigens (CFA pili) Binding to Glycophorin

This example illustrates how the 1-galactose derivatives of formula I above could be tested for their ability to inhibit CFA pili binding to glycophorin. Bacterial surface adhesion antigens such as CFA pili are a virulence factor expressed by certain enteric pathogens, including enterotoxigenic *E. coli*. These pili are important factors in bacterial attachment to cell surface receptors. Accordingly, inhibition of CFA pili binding is a useful test to determine whether a compound will inhibit the binding of a pathogenic microorganism to cell surface receptors.

Binding assays are done by coating microtitre wells with 50 μL of glycophorin (10 μg/mL) in PBS for 2 h at 37° C. The solution is removed by aspiration and replaced with 100 μL of 1% BSA in PBS containing 0.05% Tween 20 (PBST) and incubated at 37° C. for an additional 1 h. The microtitre wells are washed three times with 200 μL of PBST and then replaced with biotinylated CFA I (5 μg/mL) in 50 μL of PBS containing 0.05% BSA. After incubating for 2 h at 37° C., the binding reaction is stopped by aspirating the solutions and the plate is washed with PBST (3×200 μL). Avidin-peroxidase (50 μL of a 1/3000 dilution of a 1 mg/mL solution in PBST containing 0.05% BSA) is added and the plates are incubated for an additional 1 h. After washing the wells as described above, 100 μL of the substrate solution (0.42 mM tetramethylbenzidine (TMB) in 0.1 M sodium citrate buffer, pH 6.0, containing 0.5 μM urea peroxide) is added and the plates are incubated for 10 min at ambient temperature and the enzyme reaction stopped by adding 50 μL of 2N $H_2SO_4$. Binding assays are done in triplicate and background binding is measured in wells coated with BSA only.

Binding inhibition assays are done using oligosaccharide analogs at a concentration of 1 mg/mL in PBS. Inhibitors are pre-incubated with biotinylated CFA I pili (5 μ/mL) for 1 h at 37° C. prior to adding to glycophorin-coated microtitre wells as outlined above.

o-Nitrophenyl-β-D-galactose is utilized as a control inhibitor for these experiments. The 1-galactose derivatives of this invention are expected to inhibited CFA I pili binding to glycophorin in this assay.

From the foregoing description, various modifications and changes in the composition and method will occur to those skilled in the art. All such modifications coming within the scope of the appended claims are intended to be included therein.

What is claimed is:

1. A compound of formula I:

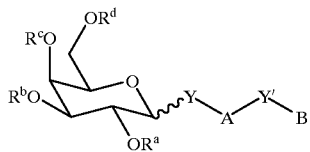

wherein

A is selected from the group consisting of arylene, cycloalkylene, cycloalkenylene, heteroarylene and divalent heterocyclic;

B is selected from the group consisting of cycloalkyl, cycloalkenyl and heterocyclic;

Y is selected from the group consisting of alkylene, substituted alkylene and —N($R^1$)—, wherein $R^1$ is selected from the group consisting of —C(O)$R^2$ and —$SO_2R^3$, wherein $R^2$ and $R^3$ are independently selected from the group consisting of alkyl, alkenyl, alkaryl, alkoxyalkyl, aryl, cycloalkyl, cycloalkenyl, heteroaryl, heterocyclic and thioalkoxyalkyl;

Y' is selected from the group consisting of oxygen, sulfur, —S(O)—, —$SO_2$—, alkylene, substituted alkylene, and —N($R^4$)—, wherein $R^4$ is selected from the group consisting of hydrogen, alkyl, alkenyl, alkaryl, alkoxyalkyl, aryl, cycloalkyl, cycloalkenyl, heteroaryl, heterocyclic, thioalkoxyalkyl, —C(O)$R^5$ and —$SO_2R^6$, wherein $R^5$ and $R^6$ are independently selected from the group consisting of alkyl, alkenyl, alkaryl, alkoxyalkyl, aryl, cycloalkyl, cycloalkenyl, heteroaryl, heterocyclic and thioalkoxyalkyl; and $R^a$, $R^b$, $R^c$ and $R^d$ are each independently selected from the group consisting of hydrogen; sulfate; —C(O)$R^7$, wherein $R^7$ is selected from the group consisting of alkyl, alkenyl, alkaryl, alkoxyalkyl, aryl, cycloalkyl, cycloalkenyl, heteroaryl, heterocyclic and thioalkoxyalkyl; and —P(O)(O$R^8$)$_2$, wherein each $R^8$ is independently selected from the group consisting of hydrogen, alkyl, alkenyl, alkaryl, alkoxyalkyl, aryl, cycloalkyl, cycloalkenyl, heteroaryl, heterocyclic and thioalkoxyalkyl;

and pharmaceutically acceptable salts thereof.

2. The compound of claim 1 wherein the compound of formula I is an α-anomer.

3. The compound of claim 1 wherein the compound of formula I is a β-anomer.

4. The compound of claim 1 wherein A is a cycloalkylene group having 5 to 7 carbon atoms.

5. The compound of claim 4 wherein A is selected from the group consisting of cyclopentylene, methylcyclopentylene, dimethylcyclopentylene, cyclohexylene, methylhexylene, dimethylcyclohexylene and cycloheptylene.

6. The compound of claim 1 wherein B is a cycloalkyl group having 4 to 7 carbon atoms.

7. The compound of claim 6 wherein B is selected from the group consisting of cyclobutyl, methylcyclobutyl, dimethylcyclobutyl, cyclopentyl, methylcyclopentyl, dimethylcyclopentyl, cyclohexyl, dimethylcyclohexyl and cycloheptyl.

8. The compound of claim 7 wherein B is cyclobutyl or dimethylcyclobutyl.

9. The compound of claim 1 wherein Y is alkylene or substituted alkylene.

10. The compound of claim 9 where Y is —$CH_2$—.

11. The compound of claim 1 wherein Y is —$N(R^1)$—.

12. The compound of claim 11 wherein Y is —$N(COCH_3)$—.

13. The compound of claim 1 wherein Y' is —NH—.

14. The compound of claim 1 wherein $R^a$, $R^b$, $R^c$ and $R^d$ are each hydrogen.

15. A pharmaceutical composition comprising from 1 to 99 weight percent of a pharmaceutically acceptable carrier and from 1 to 99 weight percent of at least one compound of formula I:

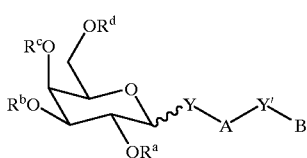

I wherein

A is selected from the group consisting of arylene, cycloalkylene, cycloalkenylene, heteroarylene and divalent heterocyclic;

B is selected from the group consisting of cycloalkyl, cycloalkenyl and heterocyclic;

Y is selected from the group consisting of alkylene, substituted alkylene and —$N(R^1)$—, wherein $R^1$ is selected from the group consisting of —$C(O)R^2$ and —$SO_2R^3$, wherein $R^2$ and $R^3$ are independently selected from the group consisting of alkyl, alkenyl, alkaryl, alkoxyalkyl, aryl, cycloalkyl, cycloalkenyl, heteroaryl, heterocyclic and thioalkoxyalkyl;

Y' is selected from the group consisting of oxygen, sulfur, —S(O)—, —$SO_2$—, alkylene, substituted alkylene, and —$N(R^4)$—, wherein $R^4$ is selected from the group consisting of hydrogen, alkyl, alkenyl, alkaryl, alkoxyalkyl, aryl, cycloalkyl, cycloalkenyl, heteroaryl, heterocyclic, thioalkoxyalkyl, —$C(O)R^5$ and —$SO_2R^6$, wherein $R^5$ and $R^6$ are independently selected from the group consisting of alkyl, alkenyl, alkaryl, alkoxyalkyl, aryl, cycloalkyl, cycloalkenyl, heteroaryl, heterocyclic and thioalkoxyalkyl; and $R^a$, $R^b$, $R^c$ and $R^d$ are each independently selected from the group consisting of hydrogen; sulfate; —$C(O)R^7$, wherein $R^7$ is selected from the group consisting of alkyl, alkenyl, alkaryl, alkoxyalkyl, aryl, cycloalkyl, cycloalkenyl, heteroaryl, heterocyclic and thioalkoxyalkyl; and —$P(O)(OR^8)_2$, wherein each $R^8$ is independently selected from the group consisting of hydrogen, alkyl, alkenyl, alkaryl, alkoxyalkyl, aryl, cycloalkyl, cycloalkenyl, heteroaryl, heterocyclic and thioalkoxyalkyl;

and pharmaceutically acceptable salts thereof.

16. The pharmaceutical composition of claim 15 wherein the compound of formula I is an α-anomer.

17. The pharmaceutical composition of claim 15 wherein the compound of formula I is a β-anomer.

18. The pharmaceutical composition of claim 15 wherein A is a cycloalkylene group having 5 to 7 carbon atoms.

19. The pharmaceutical composition of claim 18 wherein A is selected from the group consisting of cyclopentylene, methylcyclopentylene, dimethylcyclopentylene, cyclohexylene, methylhexylene, dimethylcyclohexylene and cycloheptylene.

20. The pharmaceutical composition of claim 15 wherein B is a cycloalkyl group having 4 to 7 carbon atoms.

21. The pharmaceutical composition of claim 20 wherein B is selected from the group consisting of cyclobutyl, methylcyclobutyl, dimethylcyclobutyl, cyclopentyl, methylcyclopentyl, dimethylcyclopentyl, cyclohexyl, dimethylcyclohexyl and cycloheptyl.

22. The pharmaceutical composition of claim 21 wherein B is cyclobutyl or dimethylcyclobutyl.

23. The pharmaceutical composition of claim 15 wherein Y is alkylene or substituted alkylene.

24. The pharmaceutical composition of claim 23 wherein Y is —$CH_2$—.

25. The pharmaceutical composition of claim 15 wherein Y is —$N(R^1)$—.

26. The pharmaceutical composition of claim 25 wherein Y is —$N(COCH_3)$—.

27. The pharmaceutical composition of claim 15 wherein Y' is —NH—.

28. The pharmaceutical composition of claim 15 wherein $R^a$, $R^b$, $R^c$ and $R^d$ are each hydrogen.

29. A method of ameliorating conditions associated with binding of a toxin to its receptor in an animal which method comprises administering to said animal an effective amount of a pharmaceutical composition of claim 15, wherein the compound of formula I inhibits the binding of the toxin to its receptor.

30. The method of claim 29 wherein the toxin is heat-labile enterotoxin or cholera toxin.

31. A method of ameliorating conditions associated with binding of an organism to its cell surface receptor in an animal which method comprises administering to said animal an effective amount of a pharmaceutical composition of claim 15, wherein the compound of formula I inhibits the binding of the organism to its cell surface receptor.

32. The method of claim 31 wherein the organism is *Vibrio cholerae* or an enterotoxigenic strain of *Escherichia coli*.

33. A 1-galactose derivative-containing support comprising a support having covalently bound thereto a plurality of at least one compound of formula I':

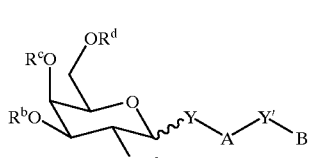

I' wherein

A is selected from the group consisting of arylene, cycloalkylene, cycloalkenylene, heteroarylene and divalent heterocyclic;

B is selected from the group consisting of cycloalkyl, cycloalkenyl and heterocyclic;

Y is selected from the group consisting of alkylene, substituted alkylene and —$N(R^1)$—, wherein $R^1$ is selected from the group consisting of —$C(O)R^2$ and —$SO_2R^3$, wherein $R^2$ and $R^3$ are independently selected from the group consisting of alkyl, alkenyl, alkaryl, alkoxyalkyl, aryl, cycloalkyl, cycloalkenyl, heteroaryl, heterocyclic and thioalkoxyalkyl;

Y' is selected from the group consisting of oxygen, sulfur, —S(O)—, —$SO_2$—, alkylene, substituted alkylene, and —N(R⁴)—, wherein R⁴ is selected from the group consisting of hydrogen, alkyl, alkenyl, alkaryl, alkoxyalkyl, aryl, cycloalkyl, cycloalkenyl, heteroaryl, heterocyclic, thioalkoxyalkyl, —C(O)R⁵ and —SO₂R⁶, wherein R⁵ and R⁶ are independently selected from the group consisting of alkyl, alkenyl, alkaryl, alkoxyalkyl, aryl, cycloalkyl, cycloalkenyl, heteroaryl, heterocyclic and thioalkoxyalkyl; and R$^a$, R$^b$, R$^c$ and R$^d$ are each independently selected from the group consisting of hydrogen; sulfate; —C(O)R⁷, wherein R⁷ is selected from the group consisting of alkyl, alkenyl, alkaryl, alkoxyalkyl, aryl, cycloalkyl, cycloalkenyl, heteroaryl, heterocyclic and thioalkoxyalkyl; and —P(O)(OR⁸)₂, wherein each R⁸ is independently selected from the group consisting of hydrogen, alkyl, alkenyl, alkaryl, alkoxyalkyl, aryl, cycloalkyl, cycloalkenyl, heteroaryl, heterocyclic and thioalkoxyalkyl;

and pharmaceutically acceptable salts thereof;

wherein one of A, B, R$^a$, R$^b$, R$^c$ or R$^d$ is covalently bound via a linking arm to the support.

34. The 1-galactose derivative-containing support of claim 33 wherein the support is a solid support.

35. The 1-galactose derivative-containing support of claim 33 wherein the compound of formula I' is an α-anomer.

36. The 1-galactose derivative-containing support of claim 33 wherein the compound of formula I' is a β-anomer.

37. The 1-galactose derivative-containing support of claim 33 wherein A is a cycloalkylene group having 5 to 7 carbon atoms.

38. The 1-galactose derivative-containing support of claim 37 wherein A is selected from the group consisting of cyclopentylene, methylcyclopentylene, dimethylcyclopentylene, cyclohexylene, methylhexylene, dimethylcyclohexylene and cycloheptylene.

39. The 1-galactose derivative-containing support of claim 33 wherein B is a cycloalkyl group having 4 to 7 carbon atoms.

40. The 1-galactose derivative-containing support of claim 39 wherein B is selected from the group consisting of cyclobutyl, methylcyclobutyl, dimethylcyclobutyl, cyclopentyl, methylcyclopentyl, dimethylcyclopentyl, cyclohexyl, dimethylcyclohexyl and cycloheptyl.

41. The 1-galactose derivative-containing support of claim 40 wherein B is cyclobutyl or dimethylcyclobutyl.

42. The 1-galactose derivative-containing support of claim 33 wherein Y is alkylene or substituted alkylene.

43. The 1-galactose derivative-containing support of claim 42 wherein Y is —CH₂—.

44. The 1-galactose derivative-containing support of claim 33 wherein Y is —N(R¹)—.

45. The 1-galactose derivative-containing support of claim 44 wherein Y is —N(COCH₃)—.

46. The 1-galactose derivative-containing support of claim 33 wherein Y' is —NH—.

47. A pharmaceutical composition comprising from 1 to 99 weight percent of a pharmaceutically acceptable carrier and from 1 to 99 weight percent of a 1-galactose derivative-containing support comprising a support having covalently bound thereto a plurality of at least one compound of formula I':

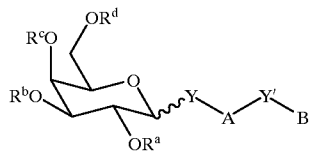

wherein

A is selected from the group consisting of arylene, cycloalkylene, cycloalkenylene, heteroarylene and divalent heterocyclic;

B is selected from the group consisting of cycloalkyl, cycloalkenyl and heterocyclic;

Y is selected from the group consisting of alkylene, substituted alkylene and —N(R¹)—, wherein R¹ is selected from the group consisting of —C(O)R² and —SO₂R³, wherein R² and R³ are independently selected from the group consisting of alkyl, alkenyl, alkaryl, alkoxyalkyl, aryl, cycloalkyl, cycloalkenyl, heteroaryl, heterocyclic and thioalkoxyalkyl;

Y' is selected from the group consisting of oxygen, sulfur, —S(O)—, —SO₂—, alkylene, substituted alkylene, and —N(R⁴)—, wherein R⁴ is selected from the group consisting of hydrogen, alkyl, alkenyl, alkaryl, alkoxyalkyl, aryl, cycloalkyl, cycloalkenyl, heteroaryl, heterocyclic, thioalkoxyalkyl, —C(O)R⁵ and —SO₂R⁶, wherein R⁵ and R⁶ are independently selected from the group consisting of alkyl, alkenyl, alkaryl, alkoxyalkyl, aryl, cycloalkyl, cycloalkenyl, heteroaryl, heterocyclic and thioalkoxyalkyl; and R$^a$, R$^b$, R$^c$ and R$^d$ are each independently selected from the group consisting of hydrogen; sulfate; —C(O)R⁷, wherein R⁷ is selected from the group consisting of alkyl, alkenyl, alkaryl, alkoxyalkyl, aryl, cycloalkyl, cycloalkenyl, heteroaryl, heterocyclic and thioalkoxyalkyl; and —P(O)(OR⁸)₂, wherein each R⁸ is independently selected from the group consisting of hydrogen, alkyl, alkenyl, alkaryl, alkoxyalkyl, aryl, cycloalkyl, cycloalkenyl, heteroaryl, heterocyclic and thioalkoxyalkyl;

and pharmaceutically acceptable salts thereof;

wherein one of A, B, R$^a$, R$^b$, R$^c$ or R$^d$ is covalently bound via a linking arm to the support.

48. The pharmaceutical composition of claim 47 wherein the support is a solid support.

49. The pharmaceutical composition of claim 47 wherein the compound of formula I' is an α-anomer.

50. The pharmaceutical composition of claim 47 wherein the compound of formula I' is a β-anomer.

51. The pharmaceutical composition of claim 47 wherein A is a cycloalkylene group having 5 to 7 carbon atoms.

52. The pharmaceutical composition of claim 51 wherein A is selected from the group consisting of cyclopentylene, methylcyclopentylene, dimethylcyclopentylene, cyclohexylene, methylhexylene, dimethylcyclohexylene and cycloheptylene.

53. The pharmaceutical composition of claim 47 wherein B is a cycloalkyl group having 4 to 7 carbon atoms.

54. The pharmaceutical composition of claim 53 wherein B is selected from the group consisting of cyclobutyl, methylcyclobutyl, dimethylcyclobutyl, cyclopentyl, methylcyclopentyl, dimethylcyclopentyl, cyclohexyl, dimethylcyclohexyl and cycloheptyl.

55. The pharmaceutical composition of claim 54 wherein B is cyclobutyl or dimethylcyclobutyl.

56. The pharmaceutical composition of claim 47 wherein Y is alkylene or substituted alkylene.

57. The pharmaceutical composition of claim 56 wherein Y is —$CH_2$—.

58. The pharmaceutical composition of claim 47 wherein Y is —$N(R^1)$—.

59. The pharmaceutical composition of claim 58 wherein Y is —$N(COCH_3)$—.

60. The pharmaceutical composition of claim 47 wherein Y' is —NH—.

61. A method of ameliorating conditions associated with binding of a toxin to its receptor in an animal which method comprises administering to said animal an effective amount of a pharmaceutical composition of claim 47, wherein the compound of formula I' inhibits the binding of the toxin to its receptor.

62. The method of claim 61 wherein the toxin is heat-labile enterotoxin or cholera toxin.

63. A method of ameliorating conditions associated with binding of an organism to its cell surface receptor in an animal which method comprises administering to said animal an effective amount of a pharmaceutical composition of claim 47, wherein the compound of formula I' inhibits the binding of the organism to its cell surface receptor.

64. The method of claim 63 wherein the organism is *Vibrio cholerae* or an enterotoxigenic strain of *Escherichia coli*.

\* \* \* \* \*